US012630501B2

(12) United States Patent
Richter-Dayan et al.

(10) Patent No.: US 12,630,501 B2
(45) Date of Patent: May 19, 2026

(54) ANTI-FIBROTIC COMPOUNDS AND USE THEREOF

(71) Applicant: HADASIT MEDICAL RESEARCH SERVICES AND DEVELOPMENT LTD., Jerusalem (IL)

(72) Inventors: Shulamit Richter-Dayan, Jerusalem (IL); Raphael Breuer, Jerusalem (IL); Rotem Sertchook, Gedera (IL)

(73) Assignee: HADASIT MEDICAL RESEARCH SERVICES AND DEVELOPMENT LTD., Jerusalem (IL)

( * ) Notice: Subject to any disclaimer, the term of this patent is extended or adjusted under 35 U.S.C. 154(b) by 1099 days.

(21) Appl. No.: 17/640,805

(22) PCT Filed: Sep. 7, 2020

(86) PCT No.: PCT/IL2020/050970
§ 371 (c)(1),
(2) Date: Mar. 4, 2022

(87) PCT Pub. No.: WO2021/044430
PCT Pub. Date: Mar. 11, 2021

(65) Prior Publication Data

US 2022/0371990 A1 Nov. 24, 2022

Related U.S. Application Data

(60) Provisional application No. 62/897,332, filed on Sep. 8, 2019.

(51) Int. Cl.

| | |
|---|---|
| ***C07C 259/06*** | (2006.01) |
| ***A61P 11/00*** | (2006.01) |
| ***C07D 209/34*** | (2006.01) |
| ***C07D 473/16*** | (2006.01) |
| ***C07D 473/18*** | (2006.01) |

(52) U.S. Cl.
CPC ............ *C07C 259/06* (2013.01); *A61P 11/00* (2018.01); *C07D 209/34* (2013.01); *C07D 473/16* (2013.01); *C07D 473/18* (2013.01)

(58) Field of Classification Search
CPC .................................................. C07C 259/06
See application file for complete search history.

(56) References Cited

U.S. PATENT DOCUMENTS

| | | | |
|---|---|---|---|
| 4,670,469 | A | 6/1987 | Schewe |
| 6,552,065 | B2 | 4/2003 | Remiszewski |
| 8,143,282 | B2 | 3/2012 | Chen |
| 2011/0300134 | A1 | 12/2011 | Van Duzer |

FOREIGN PATENT DOCUMENTS

| | | | |
|---|---|---|---|
| CN | 104098551 | A | 10/2014 |
| CN | 104744446 | A | 7/2015 |
| CN | 104761507 | A | 7/2015 |
| EP | 2671614 | A1 | 12/2013 |
| WO | 8704152 | A1 | 7/1987 |
| WO | 2008003800 | A1 | 1/2008 |
| WO | 2008006051 | A2 | 1/2008 |
| WO | 2008028065 | A2 | 3/2008 |
| WO | 2009035718 | A1 | 3/2009 |
| WO | 2009036055 | A1 | 3/2009 |
| WO | 2009036057 | A1 | 3/2009 |
| WO | 2012036168 | A1 | 3/2012 |
| WO | 2016118859 | A1 | 7/2016 |
| WO | 2021188849 | A1 | 9/2021 |

OTHER PUBLICATIONS

Lu, Weiqiang, et al. "Drug Repurposing of Histone Deacetylase Inhibitors That Alleviate Neutrophilic Inflammation in Acute Lung Injury and Idiopathic Pulmonary Fibrosis via Inhibiting Leukotriene A4 Hydrolase and Blocking LTB4 Biosynthesis." J. Medicinal Chem. (2017), 60, pp. 1817-1828. (Year: 2017).*
Akgedik et al., (2012) Effect of resveratrol on treatment of bleomycin-induced pulmonary fibrosis in rats. Inflammation 35(5): 1732-1741.
Alcaín and Villalba (2009) Sirtuin inhibitors. Expert Opin Ther Pat 19(3): 283-294.
Bijangi-Vishehsaraei et al., (2010) 4-(4-Chloro-2-methylphenoxy)-N-hydroxybutanamide (CMH) targets mRNA of the c-FLIP variants and induces apoptosis in MCF-7 human breast cancer cells. Mol Cell Biochem 342(1-2): 133-142.
Bulvik et al., (2020) SIRT1 Deficiency, Specifically in Fibroblasts, Decreases Apoptosis Resistance and Is Associated with Resolution of Lung-Fibrosis. Biomolecules 10(7): 996.
Chen et al., (2010) MolProbity: all-atom structure validation for macromolecular crystallography. Acta Crystallogr D Biol Crystallogr 66(Pt 1): 12-21.
Cohen et al., (2009) Thy1 up-regulates FasL expression in lung myofibroblasts via Src family kinases. Am J Respir Cell Mol Biol 40(2): 231-238.
Dai et al., (2018) Sirtuin activators and inhibitors: Promises, achievements, and challenges. Pharmacol Ther. Author manuscript; available in PMC Aug. 1, 2019. Published in final edited form as: Pharmacol Ther. Aug. 2018; 188: 140-154.
Gabay et al., (2013) Sirtuin 1 enzymatic activity is required for cartilage homeostasis in vivo in a mouse model. Arthritis Rheum 65(1): 159-166.
Ghosh and Chan (2016) Analysis of RNA-Seq Data Using TopHat and Cufflinks. Methods Mol Biol 1374: 339-361.
Golan-Gerstl et al., (2007) Epithelial cell apoptosis by fas ligand-positive myofibroblasts in lung fibrosis. Am J Respir Cell Mol Biol 36(3): 270-275.

(Continued)

*Primary Examiner* — John S Kenyon
(74) *Attorney, Agent, or Firm* — FULLER IP LAW LLC; Rodney J. Fuller

(57) ABSTRACT

The present invention relates to compounds, compositions and methods for treating fibrosis. In particular, compounds that inhibit or downregulate Sirtuin 1 (SIRT1) activity, which are particularly useful in the treatment of Idiopathic Pulmonary Fibrosis (IPF) are provided.

16 Claims, 12 Drawing Sheets

Specification includes a Sequence Listing.

(56) References Cited

OTHER PUBLICATIONS

Golan-Gerstl et al., (2012) Cellular FLICE-like inhibitory protein deviates myofibroblast fas-induced apoptosis toward proliferation during lung fibrosis. Am J Respir Cell Mol Biol 47(3): 271-279.
Gong et al., (2019) Apoptosis Induction byHistone Deacetylase Inhibitors in Cancer Cells: Role of Ku70. Int J Mol Sci 20(7): 1601.
Haag et al., (2011) Identification of c-FLIP(L) and c-FLIP(S) as critical regulators of death receptor-induced apoptosis in pancreatic cancer cells. Gut 60(2): 225-237.
Hu et al., (2014) Sirtuin inhibitors as anticancer agents. Future Med Chem. Author manuscript; available in PMC Apr. 3, 2015. Published in final edited form as: Future Med Chem. May 2014; 6(8): 945-966.
Idiopathic Pulmonary Fibrosis Clinical Research Network et al., (2012) Prednisone, azathioprine, and N-acetylcysteine for pulmonary fibrosis. N Engl J Med 366(21): 1968-1977.
Kerr et al., (2012) Identification of an acetylation-dependant Ku70/FLIP complex that regulates FLIP expression and HDAC inhibitor-induced apoptosis. Cell Death Differ 19(8): 1317-1327.
Kim et al., (2013) Ku70 acetylation and modulation of c-Myc/ATF4/CHOP signaling axis by SIRT1 inhibition lead to sensitization of HepG2 cells to TRAIL through induction of DR5 and down-regulation of c-FLIP. Int J Biochem Cell Biol 45(3): 711-723.
Kim et al., (2013) TopHat2: accurate alignment of transcriptomes in the presence of insertions, deletions and gene fusions. Genome Biol 14(4): R36.
Konikov-Rozenman et al., (2020) CMH-Small Molecule Docks into SIRT1, Elicits Human IPF-Lung Fibroblast Cell Death, Inhibits Ku70-deacetylation, FLIP and Experimental Pulmonary Fibrosis. Biomolecules 10(7): 997.
Korfei et al., (2019) Inhibition of Profibrotic Signaling in Primary Fibroblasts from Patients with Idiopathic Pulmonary Fibrosis (IPF) by Sirtuin-1/-2-Inhibitor Sirtinol. American Thoracic Society 2019 International Conference, C62. Fibroblast Biology, American Thoracic Society, Thematic Poster Session (May 21, 2019), Abstract No. A5352. Retrieved from URL: https://www.atsjournals.org/doi/abs/10.1164/ajrccm-conference.2019.199.1_MeetingAbstracts.A5352.
Marson et al., (2007) Structure-activity relationships of aryloxyalkanoic acid hydroxyamides as potent inhibitors of histone deacetylase. Bioorg Med Chem Lett 17(1): 136-141.
Morris et al., (2009) AutoDock4 and AutoDockTools4: Automated docking with selective receptor flexibility. J Comput Chem 30(16): 2785-2791.
Qin et al., (2017) Selective histone deacetylase small molecule inhibitors: recent progress and perspectives. Expert Opin Ther Pat 27(5): 621-636.
Seifert et al., (2012) SirT1 catalytic activity is required for male fertility and metabolic homeostasis in mice. FASEB J 26(2): 555-566.
Sener et al., (2007) Resveratrol alleviates bleomycin-induced lung injury in rats. Pulm Pharmacol Ther 20(6): 642-649.
Shetty et al., (2017) p53 and miR-34a Feedback Promotes Lung Epithelial Injury and Pulmonary Fibrosis. Am J Pathol 187(5): 1016-1034.
Song et al., (2015) Identification of long non-coding RNA involved in osteogenic differentiation from mesenchymal stem cells using RNA-Seq data. Genet Mol Res 14(4): 18268-18279.
Tanaka et al., (2002) Resistance to Fas-mediated apoptosis in human lung fibroblast. Eur Respir J 20(2): 359-368.
Trott and Olson (2010) AutoDock Vina: improving the speed and accuracy of docking with a new scoring function, efficient optimization, and multithreading. J Comput Chem 31(2): 455-461.
Villalba and Alcain (2012) Sirtuin activators and inhibitors. Biofactors. Author manuscript; available in PMC Sep. 1, 2013. Published in final edited form as: Biofactors. Sep. 2012; 38(5): 349-359.
Vukmirovic et al., (2017) Identification and validation of differentially expressed transcripts by RNA-sequencing of formalin-fixed, paraffin-embedded (FFPE) lung tissue from patients with Idiopathic Pulmonary Fibrosis. BMC Pulm Med 17(1): 15.
Wallach-Dayan et al., (2006) Bleomycin initiates apoptosis of lung epithelial cells by ROS but not by Fas/FasL pathway. Am J Physiol Lung Cell Mol Physiol 290(4): L790-L796.
Wallach-Dayan et al., (2007) Evasion of myofibroblasts from immune surveillance: a mechanism for tissue fibrosis. Proc Natl Acad Sci U S A 104(51): 20460-20465.
Wallach-Dayan et al., (2008) DNA vaccination with CD44 variant isoform reduces mammary tumor local growth and lung metastasis. Mol Cancer Ther 7(6): 1615-1623.
Wallach-Dayan et al., (2015) Cutting edge: FasL(+) immune cells promote resolution of fibrosis. J Autoimmun 59: 67-76.
Wilson et al., (2013) Lentiviral delivery of RNAi for in vivo lineage-specific modulation of gene expression in mouse lung macrophages. Mol Ther 21(4): 825-833.
Woltmann et al., (2014) Systematic pathway enrichment analysis of a genome-wide association study on breast cancer survival reveals an influence of genes involved in cell adhesion and calcium signaling on the patients' clinical outcome. PLoS One 9(6): e98229.
Wood et al., (2010) Selective inhibition of histone deacetylases sensitizes malignant cells to death receptor ligands. Mol Cancer Ther 9(1): 246-256.
Wu et al., (2015) Silent information regulator 1 (SIRT1) ameliorates liver fibrosis via promoting activated stellate cell apoptosis and reversion. Toxicol Appl Pharmacol 289(2): 163-176.
Yoon et al., (2019) HDAC Inhibitors: Therapeutic Potential in Fibrosis-Associated Human Diseases. Int J Mol Sci 20(6): 1329.
You and Steegborn (2018) Structural Basis of Sirtuin 6 Inhibition by the Hydroxamate Trichostatin A: Implications for Protein Deacylase Drug Development. J Med Chem 61(23): 10922-10928.
Zeng et al., (2017) Activation and overexpression of Sirt1 attenuates lung fibrosis via P300. Biochem Biophys Res Commun 486(4): 1021-1026.
Zerr et al., (2016) Sirt1 regulates canonical TGF-β signalling to control fibroblast activation and tissue fibrosis. Ann Rheum Dis 75(1): 226-233.
CAS Registry No. 1027259-65-9; CA Index Name: Benzo[b]thiophene-3-carboxamide, 2-[(cyclopropylcarbonyl) amino]-6-[2-(hydroxyamino)-2-oxoethoxy]-; Entered STN: Jun. 11, 2008. Jun. 11, 2008 (Jun. 11, 2008).
CAS Registry No. 1367826-06-9; CA Index Name: Butanamide, N-hydroxy-4-(8-quinolinyloxy)-; Entered STN: Apr. 13, 2012. Apr. 13, 2012 (Apr. 13, 2012).

* cited by examiner

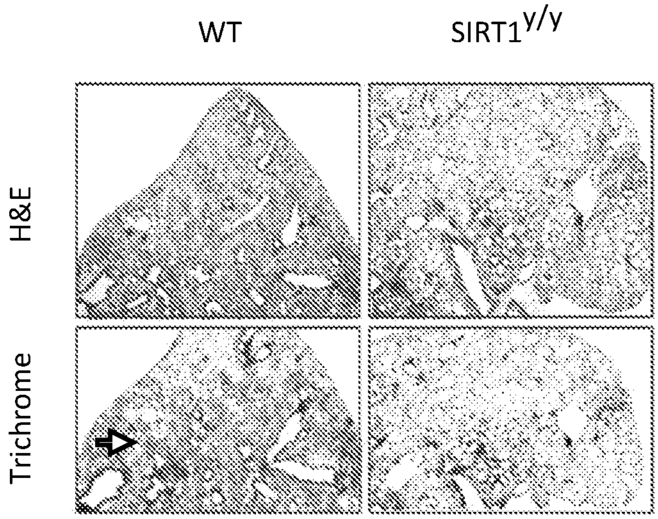
Figure 3D
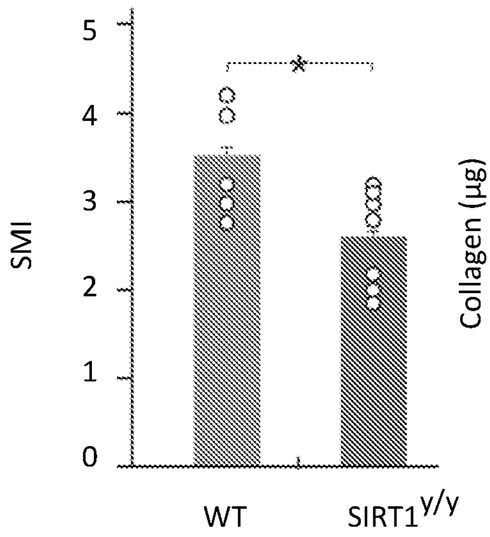
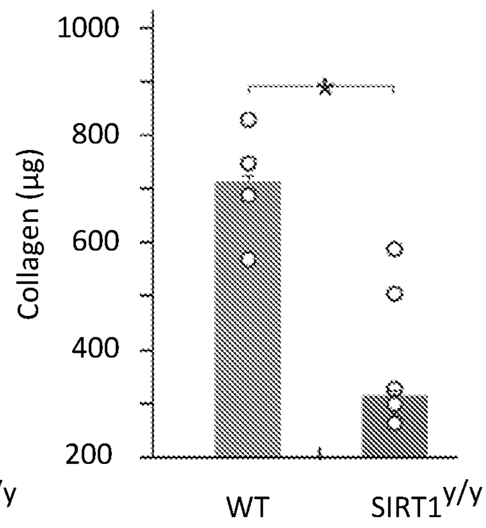
Figure 3E
Figure 3F

CMH – treatment of
BLM-induced

BLM(OA)    CMH 30μM    sacrifice
(0.05 mU)    or Vehicle

Day 0    Day 6    Day 14

Assay

FLIP, SIRT1 and Ku-70 acetylation

Lung Fibrosis & Collagen accumulation
mouse survival

Vehicle    CMH

SIRT1

FLIP

Vehicle CMH

IP:Ku-70
IB:SIRT1

GAPDH

O.D ratio    1.2    0.6

Vehicle CMH

IP:Ku-70

IB:Pan-Acetyl

GAPDH

O.D ratio    0.1    0.91

SEQUENCE LISTING

```
<160> NUMBER OF SEQ ID NOS: 2

<210> SEQ ID NO 1
<211> LENGTH: 67
<212> TYPE: DNA
<213> ORGANISM: Artificial Sequence
<220> FEATURE:
<223> OTHER INFORMATION: synthetic oligonucleotide

<400> SEQUENCE: 1

cgcgtccccg aatagacttg aacacaaatt caagagattt gtgttcaagt ctattctttt     60
```

-continued tggaaat 67

<210> SEQ ID NO 2
<211> LENGTH: 65
<212> TYPE: DNA
<213> ORGANISM: Artificial Sequence
<220> FEATURE:
<223> OTHER INFORMATION: Synthetic oligonucleotide

<400> SEQUENCE: 2
aggggcttat ctgaacttgt gtttaagttc tctaaacaca agttcagata agaaaaacct 60
ttagc 65

ANTI-FIBROTIC COMPOUNDS AND USE THEREOF

CROSS-REFERENCE TO RELATED APPLICATIONS

This application is the U.S. National Stage of International Patent Application No. PCT/IL2020/050970, filed on Sep. 7, 2020, which claims the benefit of and priority to U.S. Provisional Patent Application No. 62/897,332, filed on Sep. 8, 2019, the contents of each of which are hereby incorporated by reference in their entireties.

INCORPORATION-BY-REFERENCE OF MATERIAL ELECTRONICALLY FILED

Incorporated by reference in its entirety herein is a computer-readable nucleotide/amino acid sequence listing submitted concurrently herewith and identified as follows: One 900 byte ASCII (text) file named "Seq_List" created on Sep. 6, 2020.

FIELD OF THE INVENTION

The present invention relates to compounds and methods for the treatment of pulmonary fibrosis and other fibrotic disorders.

BACKGROUND OF THE INVENTION

Fibrosis is a condition characterized by an abnormal accumulation of fibroblasts within a tissue/organ which results in structural alterations including thickening, stiffening, and scarring of said tissue/organ. Progressive fibrosis in essential organs such as the kidneys, liver, and lungs may cause major damage to these organs ultimately leading to their loss of function.

Idiopathic Pulmonary Fibrosis (IPF) is a progressive lung disease of unknown etiology, predominantly affecting the elderly population. The disease involves epithelial injury and activation, lack of tissue regeneration, and formation of distinctive subepithelial fibroblast/myofibroblast foci with excessive extracellular matrix accumulation. These pathological processes usually lead to progressive and irreversible changes in the lung architecture, resulting in respiratory insufficiency with life expectancy of 3-5 years after diagnosis.

Attempts to develop anti-fibrotic agents for the treatment of various disorders have been reported. However, many patients do not respond to available treatments for fibrotic disorders, and long-term treatment is limited by toxicity and side effects. For example, glucocorticoids or tyrosine kinase inhibitors are prescribed for pulmonary fibrosis, but the therapeutic outcomes are still limited. Most patients suffer from progressive deterioration of pulmonary function despite conventional treatment regimens (Yoon et al., Int. J. Mol. Sci. 20: 1329-1343, 2019). Treatments aimed at reversing the fibrosis are usually too toxic for long-term use (e.g. corticosteroids, penicillamine) or have no proven efficacy (e.g. colchicine). With respect to lung fibrosis, treatments aimed at inhibiting the immune response are not only ineffective, but were even shown to increase mortality in IPF (Raghu et al., N Engl J Med 2012; 366(21): 1968-77). Further, new drugs once considered promising have also failed (e.g. Bosetan, Sildenafil, Etanercept, Imatinib). While two drugs recently approved by the FDA for IPF, namely Pirfenidone and Nintedanib, were found to attenuate the progression of fibrosis and the exacerbation of some of the symptoms, patients still retain fibrotic pathologies in their lungs, and their disease does not reverse. Therefore, a need remains for developing therapeutic modalities aimed at reducing fibrosis.

Cellular, Fas-associated death domain-like, interleukin-1-converting enzyme, (FLICE)-Like Inhibitory Protein, also known as c-FLIP, FLIP, CASP8, FADD-like apoptosis regulator and cFLAR, is a regulator of cell death receptor-induced apoptosis. FLIP was first described as a viral protein (v-FLIP) that inhibits Fas- and TNF-mediated apoptosis. Like viral FLIP, cellular FLIP competitively inhibits the binding of caspase-8 to Fas, and other cell death receptor complexes and blocks their signaling pathway of apoptosis. It has been shown that epithelial cells under Epithelial Mesenchymal Transition (EMT) or myofibroblasts from lungs with active fibrosis over-express FLIP thereby diverting Fas signaling from apoptosis to proliferation (Golan-Gerstl et al., Am. J. Respir. Cell Mol. Biol., 47(3):271-9, 2012, and Tanaka et. al., Eur. Respir. J., 20: 359-368, 2002). The cells were shown to acquire an "immune-privilege-like" phenotype (Wallach-Dayan et al., PNAS, 104(51):20460-5, 2007), thus allowing their escape from immune surveillance and unremitted accumulation.

One of the pharmacological agents identified as a modulator of FLIP-mediated pathways is the small molecule CMH (4-(4-chloro-2-methylphenoxy)-N-hydroxybutanamide, also known as Droxinostat). In breast cancer cells and pancreatic cancer cells, CMH was found to downregulate FLIP expression and increase apoptosis via inhibition of the class II deacetylase HDAC-8 (Bijangi-Vishehsaraei et al., Mol. Cell Biochem. 342: 133-142, 2010; Haag et al., Gut 60: 225-237, 2011). Selective inhibition of HDAC isoforms HDAC3, HDAC6, and HDAC8 was found in prostate cancer cells, while other isoforms including HDAC1, HDAC2, HDAC4, HDACS, HDAC7, HDAC9, and HDAC10 were not inhibited (Wood et al. Mol. Cancer Ther. 9(1):246-56, 2010). The effects of CMH in non-malignant cells are not fully elucidated. It was recently found that CMH treatment was associated with FLIP downregulation and attenuation of fibrosis in a murine experimental model.

Histone deacetylases (HDACs) are a group of enzymes that regulate gene transcription by deacetylation of histones and regulate protein stability and function by deacetylation of non-histone proteins. Overexpression of HDACs is found in some types of tumors and predicts poor prognosis. Eighteen HDACs have been identified in mammals and are divided into four classes. HDAC1, -2, -3, and -8 are class I HDACs. HDAC4, -5, -6, -7, -9, and -10 are class II HDACs. The Sirtuin family (Sirt1-7) are classified as class III HDAC. HDAC11 is the only member of class IV HDAC. Class I, II, and IV HDACs require zinc ions to deacetylate their substrate and share a conserved functional deacetylation domain, and could thus be simultaneously inhibited by a group of pan-HDAC inhibitors. Unlike zinc-dependent HDACs, class III HDACs do not share homology with other classes HDACs and are not inhibited by generic HDAC inhibitors (HDACi). Rather, Sirtuins require NAD to execute deacetylation, and can be suppressed by nicotinamides (Gong et al., Int. J. Mol. Sci. 20: 1601-1615, 2019; and Yoon et al., Int. J. Mol. Sci. 20: 1329-1343, 2019).

Deacetylation of histones has been considered as the main function of HDACs. In addition, more than 50 non-histone proteins have been reported to be the substrates of HDACs, including e.g. p53, NF-κB, STATS, Hsp90, Akt, and Ku70. Ku70 is a DNA repair factor involved in double-strand break repair. Many acetylation sites of lysine residues in Ku70, including k539, k542, k544, k553, k556, k317, k331, and k338, have been found. Ku70 binds to the cytosolic Bax, Mcl-1, and c-FLIP to increase their stability and protect cells from apoptosis (Gong et al., Int. J. Mol. Sci. 20: 1601-1615, 2019). Ku70-deacetylation stabilized FLIP and prevented cell death in colon cancer cells (Kerr et al., Cell Death Differ. 19: 1317-1327, 2012). In hepatoma cells, SIRT1 downregulation increased Ku70-acetylation, and promoted FLIP downregulation (Kim et al., Int. J. Biochem. Cell Biol. 45: 711-723, 2013).

A group of small-molecular HDACi has been developed as cancer therapeutics, with Vorinostat (SAHA), Romidepsin (FK228), Belinostat (PXD-101), Panobinostat (LBH-589), and Chidamide being approved for clinical use in the treatment of cutaneous T-cell lymphoma, peripheral T-cell lymphoma or multiple myeloma. SAHA, Belinostat, and LBH-589 are pan-HDACis. Romidepsin is a selective inhibitor of class I HDACs. Chidamide selectively inhibits class I HDACs and HDAC10. None of the five inhibitors inhibit the family of SIRTs and none have been extended to treat other types of cancer. These inhibitors have considerable and potentially fatal side effects and toxicities that restrict their use (Gong et al., Int. J. Mol. Sci. 20: 1601-1615, 2019).

Various clinical trials have been undertaken to expand the clinical indication of approved HDACis or even de novo inhibitors for solid tumors. However, the overall survival benefits were quite limited. A number of research groups have suggested a role for certain HDACs in various diseases and disease models, inter alia in fibrosis-associated diseases. However, it was found that multiple HDACs may be involved in multiple human diseases, and that two HDACs or more may play opposite roles in the development of a single disease. Due to the marked unwanted effects and potentially fatal side effects associated with currently available HDACis, their use remains restricted to severe hematomalignancies. Attempts at developing more specific HDACis have also been reported. However, only a few specific compounds have been developed to date; the high structural similarities between various HDACs and the insufficient understanding of the relevant mechanisms and pathways involved are limiting factors in the development of such compounds (Yoon et al., Int. J. Mol. Sci. 20: 1329-1343, 2019). HDAC inhibitors have been disclosed, for example, in U.S. Pat. Nos. 6,552,065; 8,143,282; and U.S. 2011/300134.

Despite the identification of Ku70 as a negative modulator of apoptosis and its regulation by acetylation/deacetylation, specific HDACis that inhibit its function have not yet been developed as therapeutic drugs for any indication. Further studies are needed to determine the specific HDAC to be used and for designing appropriate selective HDAC inhibitors. In addition, the role of Ku70 in the context of the relevant cell types and indications remains to be examined. In this regard, it is noted that Ku70 knockdown showed selective apoptotic effects in neuroblastoma cells but not in HEK293 and Hela tumor cells. The reasons for this difference are not fully understood, and have been suggested to rely on the amount of Ku70 bound to Bax and the levels of other antiapoptotic proteins in different cancer cells (Gong et al., Int. J. Mol. Sci. 20: 1601-1615, 2019).

SIRT1 is a multifunctional protein shown to perform a wide variety of functions in biological systems. SIRT1 has been reported to be involved in fibrosis and aging of various organs (Wu et al., Toxicol. Appl. Pharmacol. 289: 163-176, 2015; and Zen et al., Ann. Rheum. Dis. 75: 226-233, 2016), with particularly contradictory results in lung fibrosis (Akgedik et al., Inflamm. 35: 1732-1741, 2012; Sener et al., Pulm. Pharmacol. Ther. 20: 642-649, 2007; Shetty et al., Am. J. Pathol. 187: 1016-1034, 2017; and Zeng et al., Biochem. Biophys. Res. Commun. 486: 1021-1026, 2017). Differences may result from assessment at different time points of fibrosis following injury and/or of SIRT1 activity vs. expression. Notably, of the various SIRT1 modulators reported, compounds approved for clinical use, including in the treatment of disorders associated with fibrosis, are mostly SIRT1 agonists (e.g. metformin, resveratrol, SRT-3025 and GSK-2245840), and it is generally considered beneficial to activate SIRT1 in the management of fibrotic disorders. EP 2671614 relates to a compound that increases the cellular activity of SIRT1, and one or more pharmaceutically acceptable excipients, for use in the treatment of an inflammatory disorder, inter alia, idiopathic pulmonary fibrosis. WO 2012/036168 relates to a composition useful for treating muscular dystrophy and suppressing fibrosis of skeletal muscle in muscular dystrophy, comprising a Sirtuin 1 activator. WO 2008/028065 relates to an agent that activates a class III histone deacetylase, useful for reducing cardiac hypertrophy or fibrosis, fetal gene activation, myocyte cell-death or ventricular dilation.

Konikov-Rozenman et al. (Biomolecules 2020, 10, 997), to some of the present inventors, published after the priority date of the present application, discloses that CMH-small molecule docks into SIRT1, elicits human IPF-lung fibroblast cell death, inhibits Ku70-deacetylation, FLIP and experimental pulmonary fibrosis. Another publication by the inventors and coworkers (Bulvik et al., Biomolecules 2020, 10, 996), reports that SIRT1 deficiency, specifically in fibroblasts, decreases apoptosis resistance and is associated with resolution of lung-fibrosis.

U.S. Pat. No. 4,670,469 relates to hydroxamic acids, pharmaceutical preparations containing the same, new ω(2'-naphthoxy)-alkylhydroxamic acids as well as a process for their production. The compounds are useful in human and veterinary medicine as medicaments the active principal of which is the inhibition of lipoxygenase. WO 87/04152 relates to certain aryl derivatives having lipoxygenase and cyclooxygenase inhibiting properties for use in a method of treatment of the human or animal body by surgery or therapy or of diagnosis practiced on the human or animal body.

There is an unmet need for new therapeutic approaches for treating fibrotic disorders and in particular lung fibrosis and conditions associated therewith including IPF.

SUMMARY OF THE INVENTION

The present invention is directed to the treatment and reduction of fibrosis. More specifically, embodiments of the invention provide compositions and methods useful for the treatment of fibrotic disorders, employing the use of compounds that inhibit or downregulate Sirtuin 1 (SIRT1) activity, including in particular in fibroblasts. The invention further provides potent anti-fibrotic compounds that are particularly useful in the treatment of Idiopathic Pulmonary Fibrosis (IPF).

The present invention is based, in part, on the unexpected discoveries that CMH (Droxinostat) acts as a previously unrecognized SIRT1 inhibitor that docks into SIRT1 lysine binding-site and inhibits Ku70 deacetylation, and destabilizes Ku70/FLIP complex in IPF-lung myofibroblasts. CMH is further disclosed herein to alter apoptosis pathways regulated by SIRT1 and Ku70 in human IPF-lung myofibroblasts, and to inhibit lung myofibroblast SIRT1, Ku70-deacetylation, Ku70/FLIP complex, FLIP expression, and fibrosis evolution in bleomycin (BLM)-treated mice. The invention is further based, in part, on the discovery of surprisingly effective anti-fibrotic compounds, characterized by improved pharmacokinetic properties. Thus, provided herein are compounds, compositions and methods for the treatment and management of fibrosis and fibrotic disorders.

In particular, compounds in accordance with embodiments of the invention downregulate deacetylase activity, specifically in IPF lung myofibroblasts. In other embodiments, the invention relates to compounds that exhibit enhanced efficacy in the treatment and management of fibrosis while exerting desirable pharmacokinetic properties.

In various aspects and embodiments, the invention relates to compounds represented by the structure Formula X, as follows:

Formula X

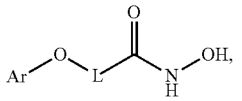

wherein L is a linker selected from the group consisting of $C_1$-$C_{10}$ alkylene, $C_2$-$C_{10}$ alkenylene, and $C_2$-$C_{10}$ alkynylene, and Ar is selected from the group consisting of:

phenyl substituted with at least one of methyl, methoxy, amido, amino, and nitro;

$C_{10}$-$C_{18}$ fused bicyclic aryl optionally substituted with at least one of hydroxy, amido, alkylamido, amino, alkylamino, carboxyl, $CH_2CH_2OH$, and $CH_2CH_2OCH_2CH_2OH$; and $C_5$-$C_9$ fused bicyclic heteroaryl optionally substituted with at least one of hydroxy, amido, alkylamido, amino, alkylamino, carboxyl, $C_1$-$C_4$ alkyl, $C_1$-$C_4$ alkoxy, halogen, haloalkyl, nitro, cyano, $CH_2CH_2OH$, and $CH_2CH_2OCH_2CH_2OH$, provided that when Ar is $C_5$-$C_9$ fused bicyclic heteroaryl substituted with methoxy and amino, then the amino is not an aniline group;

including salts, hydrates, solvates, polymorphs, optical isomers, geometrical isomers, enantiomers, diastereomers, and mixtures thereof. Each possibility represents a separate embodiment.

According to a first aspect, there is provided a pharmaceutical composition comprising a therapeutically effective amount of a compound X as disclosed hereinabove, for use in treating or inhibiting pulmonary fibrosis in a subject in need thereof.

According to a second aspect, there is provided a method of treating or inhibiting pulmonary fibrosis in a subject in need thereof, the method comprising administering to the subject a pharmaceutical composition comprising a therapeutically effective amount of a compound of Formula X as disclosed hereinabove.

In one embodiment of the first and second aspects, the fibrosis is associated with IPF. In another embodiment, treatment comprises alleviating a symptom of pulmonary fibrosis in said subject. In yet another embodiment, treatment comprises downregulation of SIRT1-mediated deacetylase activity. In further embodiments, treatment comprises inhibition of SIRT1-mediated lysine residue deacetylation on Ku70. In other embodiments, the compound of Formula X is capable of specifically binding to a binding pocket on SIRT 1 protein comprising at least one of $Val^{412}$ (main chain) and $His^{363}$ (side chain).

In some embodiments, L is a $C_1$-$C_{10}$ alkylene. In other embodiments, L is a $C_2$-$C_6$ alkylene. In yet other embodiments, L is a $C_2$-$C_4$ alkylene. In further embodiments, L is a $C_2$-$C_5$ alkylene. In other embodiments, L is a $C_4$-$C_6$ alkylene. In yet other embodiments, L is a $C_4$-$C_5$ alkylene. In one embodiment, L is a $C_4$ alkylene. In additional embodiments, L is a $C_6$ alkylene.

According to certain embodiments, Ar is a phenyl substituted with one substituent selected from methoxy, methyl, amido, amino, and nitro. Each possibility represents a separate embodiment. In various embodiments, Ar is a phenyl substituted with one substituent selected from methoxy, methyl, amido, amino, and nitro, wherein the substituent is in para position. Each possibility represents a separate embodiment. In one embodiment, L is a $C_6$ alkylene and Ar is a phenyl substituted with methoxy. In another embodiment, L is a $C_4$ alkylene and Ar is tolyl. In yet another embodiment, L is a $C_4$ alkylene and Ar is phenyl substituted with nitro, amino, or amido. Each possibility represents a separate embodiment. In other embodiments, Ar is a $C_{10}$ fused bicyclic aryl, namely a naphthyl. In further embodiments, L is a $C_2$-$C_6$ alkylene and Ar is a naphthyl. In other embodiments, L is a $C_2$-$C_5$ alkylene and Ar is a naphthyl. In yet other embodiments, L is a $C_4$-$C_5$ alkylene and Ar is a naphthyl. In additional embodiments, Ar is $C_5$-$C_9$ fused bicyclic heteroaryl substituted with at least one of methoxy, amido, and amino, provided that when Ar is substituted with methoxy and amino, then the amino is not an aniline group. In particular embodiments, L is a $C_2$-$C_4$ alkylene and Ar is $C_5$-$C_9$ fused bicyclic heteroaryl substituted with at least one of methoxy, amido, and amino, provided that when Ar is substituted with methoxy and amino, then the amino is not an aniline group.

In various embodiments, the compound represented by the structure of Formula X is selected from the group consisting of Formulae 1-18 below:

Formula 1

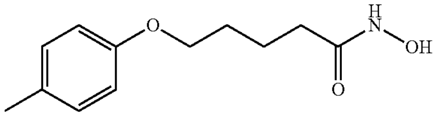

Formula 2

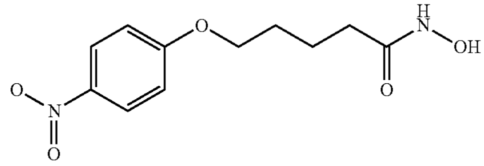

Formula 3

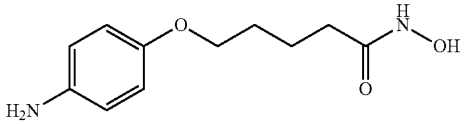

Formula 4

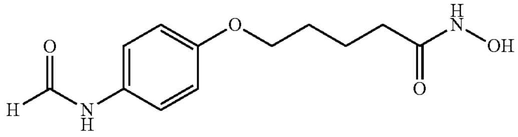

-continued

Formula 5

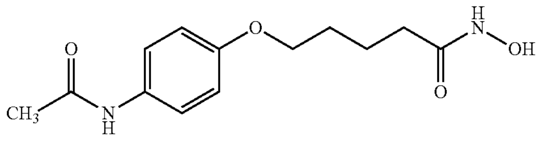

Formula 6

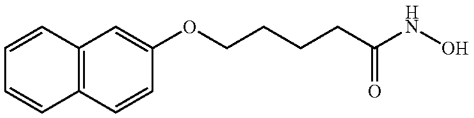

Formula 7

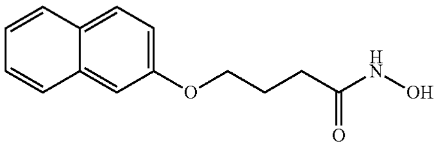

Formula 8

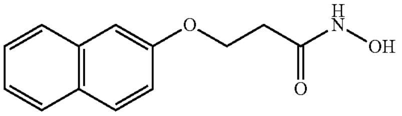

Formula 9

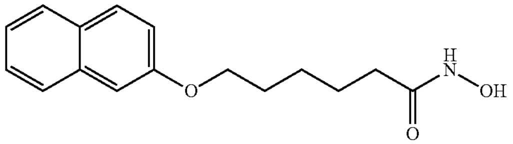

Formula 10

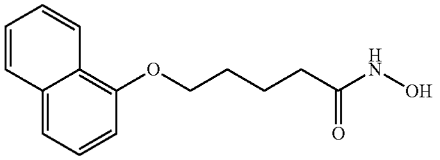

Formula 11

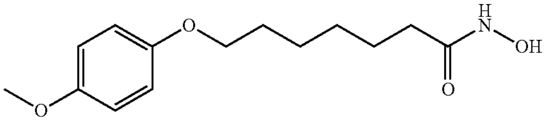

Formula 12

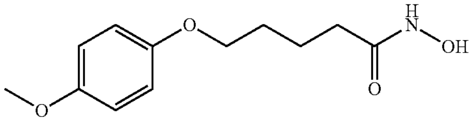

Formula 13

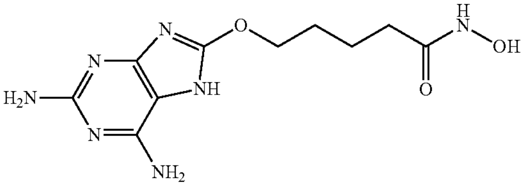

-continued

Formula 14

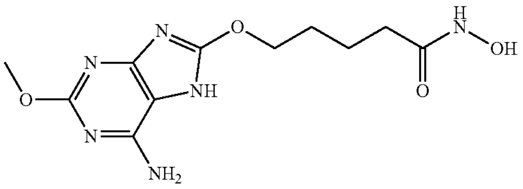

Formula 15

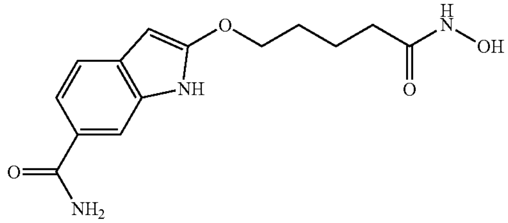

Formula 16

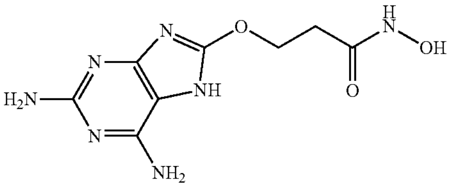

Formula 17

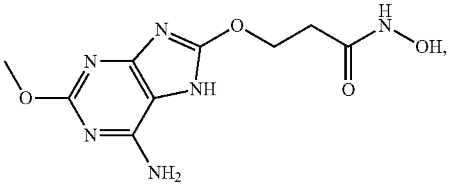

and

Formula 18

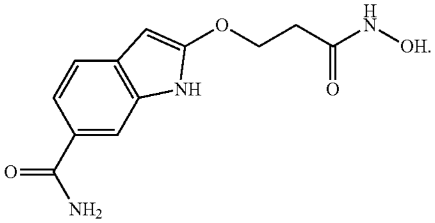

Each possibility represents a separate embodiment. In one embodiment, the compound represented by the structure of Formula X is a compound of Formula 6 or 12. Each possibility represents a separate embodiment. In another embodiment, the compound represented by the structure of Formula X is a compound of any one of Formula 1 to 5, with each possibility representing a separate embodiment. In yet another embodiment, the compound represented by the structure of Formula X is a compound of any one of Formula 6 to 12, with each possibility representing a separate embodiment. In additional embodiments, the compound represented by the structure of Formula X is a compound of any one of Formula 13 to 18, with each possibility representing a separate embodiment.

In some embodiments, the pharmaceutical composition further comprises a pharmaceutically acceptable carrier or excipient. In one embodiment, the pharmaceutically acceptable carrier or excipient comprises at least one of a binder, a filler, a diluent, a surfactant or emulsifier, a glidant or lubricant, a buffering or pH adjusting agent, a tonicity enhancing agent, a wetting agent, a preservative, an antioxidant, a flavoring agent, a colorant, and a mixture or combination thereof. Each possibility represents a separate embodiment. In one particular embodiment, the pharmaceutically acceptable carrier is a lipid carrier.

In other embodiments, the pharmaceutical composition is in a form selected from the group consisting of tablet, pill, capsule (e.g. soft or hard gelatin capsule), pellets, granules, powder, a wafer, coated or uncoated beads, lozenge, sachet, cachet, elixir, an osmotic pump, a depot system, an iontophoretic system, a patch, suspension, dispersion, emulsion, solution, syrup, aerosol, oil, ointment, suppository, a gel, and a cream. Each possibility represents a separate embodiment. In further embodiments, the pharmaceutical composition is formulated (or adapted) for administration via a route selected from the group consisting of intratracheal, intrabronchial, intra-alveolar, oral, topical, transdermal, intraarterial, intranasal, intraperitoneal, intramuscular, subcutaneous, and intravenous. In another embodiment of the methods of the invention, administration is performed in a route selected from the group consisting of intratracheal, intrabronchial, intra-alveolar, oral, topical, transdermal, intra-arterial, intranasal, intraperitoneal, intramuscular, subcutaneous, and intravenous. Each possibility represents a separate embodiment. In certain advantageous embodiments, for example when the treatment of pulmonary fibrosis is contemplated, the pharmaceutical composition is formulated for (or administered by) intratracheal, intrabronchial, or intra-alveolar administration. In a particular embodiment said administration is intratracheal.

According to some aspects and embodiments, there is provided a compound represented by the structure of Formula X, wherein L is a $C_2$-$C_6$ alkylene, and Ar is a $C_5$-$C_9$ fused bicyclic heteroaryl optionally substituted with at least one of hydroxy, amido, alkylamido, amino, alkylamino, carboxyl, $C_1$-$C_4$ alkyl, $C_1$-$C_4$ alkoxy, halogen, haloalkyl, nitro, cyano, $CH_2CH_2OH$, and $CH_2CH_2OCH_2CH_2OH$, provided that when Ar is substituted with methoxy and amino, then the amino is not an aniline group; including salts, hydrates, solvates, polymorphs, optical isomers, enantiomers, diastereomers, and mixtures thereof. Each possibility represents a separate embodiment.

According to various aspects and embodiments, there is provided a compound represented by the structure of Formula X, wherein L is a $C_2$-$C_6$ alkylene, and Ar is a $C_5$-$C_9$ fused bicyclic heteroaryl optionally substituted with at least one of hydroxy, amido, alkylamido, amino, alkylamino, carboxyl, $C_1$-$C_4$ alkyl, $C_1$-$C_4$ alkoxy, nitro, $CH_2CH_2OH$, and $CH_2CH_2OCH_2CH_2OH$, provided that when Ar is substituted with methoxy and amino, then the amino is not an aniline group; including salts, hydrates, solvates, polymorphs, optical isomers, enantiomers, diastereomers, and mixtures thereof. Each possibility represents a separate embodiment.

In further aspects and embodiments, there is provided a compound represented by the structure of Formula X, wherein L is a $C_2$-$C_6$ alkylene, and Ar is a $C_5$-$C_9$ fused bicyclic heteroaryl optionally substituted with at least one of methoxy, amino and amido, provided that when Ar is substituted with methoxy and amino, then the amino is not an aniline group; including salts, hydrates, solvates, polymorphs, optical isomers, enantiomers, diastereomers, and mixtures thereof. Each possibility represents a separate embodiment. In some embodiments, the compound represented by the structure of Formula X is a compound of any one of Formula 13 to 18, with each possibility representing a separate embodiment. In specific embodiments, there is provided a compound represented by the structure of Formula 15, including salts, hydrates, solvates, polymorphs, and mixtures thereof.

In other aspects and embodiments, there is provided a compound represented by the structure of Formula X, wherein L is a $C_4$ alkylene, and Ar is phenyl substituted with at least one of methyl, amido, amino, and nitro; including salts, hydrates, solvates, polymorphs, optical isomers, enantiomers, diastereomers, and mixtures thereof. Each possibility represents a separate embodiment. In one embodiment, Ar is phenyl substituted with one substituent selected from methyl, amido, amino, and nitro. Each possibility represents a separate embodiment. In another embodiment, the substituent is in para position. In some embodiments, the compound represented by the structure of Formula X is a compound of any one of Formula 1 to 5, with each possibility representing a separate embodiment.

In particular aspects and embodiments, there is provided a compound represented by the structure of any one of Formulae 1, 2, 3, 4, 5, 13, 14, 15, 16, 17, and 18; including salts, hydrates, solvates, polymorphs, and mixtures thereof. Each possibility represents a separate embodiment. In other aspects and embodiments, the compound is represented by the structure of any one of Formulae 13, 14, 15, 16, 17, and 18; including salts, hydrates, solvates, polymorphs, and mixtures thereof. Each possibility represents a separate embodiment.

In various embodiments, there is provided a pharmaceutical composition comprising a therapeutically effective amount of a compound represented by the structure of Formula X wherein L is a $C_2$-$C_6$ alkylene, and Ar is a $C_5$-$C_9$ fused bicyclic heteroaryl optionally substituted with at least one of hydroxy, amido, alkylamido, amino, alkylamino, carboxyl, $C_1$-$C_4$ alkyl, $C_1$-$C_4$ alkoxy, halogen, haloalkyl, nitro, cyano, $CH_2CH_2OH$, and $CH_2CH_2O$ $CH_2CH_2OH$, provided that when Ar is substituted with methoxy and amino, then the amino is not an aniline group, including salts, hydrates, solvates, polymorphs, optical isomers, enantiomers, diastereomers, and mixtures thereof; or a compound of any one of Formulae 1 to 5 and/or 13 to 18 including salts, hydrates, solvates, polymorphs, and mixtures thereof, and a pharmaceutically acceptable carrier or excipient. In some embodiments, the pharmaceutically acceptable carrier or excipient comprises at least one of a binder, a filler, a diluent, a surfactant or emulsifier, a glidant or lubricant, a buffering or pH adjusting agent, a tonicity enhancing agent, a wetting agent, a preservative, an antioxidant, a flavoring agent, a colorant, and a mixture or combination thereof. Each possibility represents a separate embodiment. In other embodiments, the pharmaceutical composition is in a form selected from the group consisting of tablet, pill, capsule, pellets, granules, powder, a wafer, coated or uncoated beads, lozenge, sachet, cachet, elixir, an osmotic pump, a depot system, an iontophoretic system, a patch, suspension, dispersion, emulsion, solution, syrup, aerosol, oil, ointment, suppository, a gel, and a cream. Each possibility represents a separate embodiment. In yet other embodiments, the pharmaceutical composition is formulated for administration via a route selected from the group consisting of intratracheal, intrabronchial, intra-alveolar, oral, topical, transdermal, intra-arterial, intranasal, intraperitoneal, intramuscular, subcutaneous, and intravenous. Each possibility represents a separate embodiment. In certain embodiments, the pharmaceutical composition is useful as a medicament. In other embodiments, the pharmaceutical composition is useful in the management of fibrosis and conditions associated therewith, as disclosed herein. In another embodiment said pharmaceutical composition is for use in treating or inhibiting pulmonary fibrosis in a subject in need thereof. In another embodiment the fibrosis is associated with IPF. In another embodiment treating comprises alleviating a symptom of pulmonary fibrosis in said subject. In another embodiment said composition is for use in treating a condition associated with pulmonary fibrosis in a subject in need thereof, wherein the treatment comprises alleviating a symptom of pulmonary fibrosis in said subject.

In another aspect, there is provided a method for treating or inhibiting fibrosis in a subject in need thereof, the method comprising administering to the subject a composition comprising a therapeutically effective amount of a compound represented by the structure of Formula X as defined herein. In some embodiments, the compound is as disclosed herein, wherein each possibility represents a separate embodiment of the invention. In another aspect, there is provided a method for treating a fibrotic disorder in a subject in need thereof, the method comprising administering to the subject a composition comprising a therapeutically effective amount of a compound represented by the structure of Formula X as defined herein. In various embodiments, the compound is as disclosed herein, wherein each possibility represents a separate embodiment of the invention.

In another aspect, there is provided a method for treating a condition associated with pulmonary fibrosis in a subject in need thereof, the method comprising administering to the subject a composition comprising a therapeutically effective amount of a compound represented by the structure of Formula X as defined herein. In another aspect there is provided a method for treating a condition associated with pulmonary fibrosis in a subject in need thereof, the method comprising administering to the subject a composition comprising a therapeutically effective amount of a compound represented by the structure of Formula X, wherein L is a $C_2$-$C_6$ alkylene, and Ar is a $C_5$-$C_9$ fused bicyclic heteroaryl optionally substituted with at least one of hydroxy, amido, alkylamido, amino, alkylamino, carboxyl, $C_1$-$C_4$ alkyl, $C_1$-$C_4$ alkoxy, halogen, haloalkyl, nitro, cyano, $CH_2CH_2OH$, and $CH_2CH_2O$ $CH_2CH_2OH$, provided that when Ar is substituted with methoxy and amino, then the amino is not an aniline group, including salts, hydrates, solvates, polymorphs, optical isomers, enantiomers, diastereomers, and mixtures thereof; or a compound of any one of Formulae 1 to 5 or 13 to 18 including salts, hydrates, solvates, polymorphs, and mixtures thereof, and wherein the treatment comprises alleviating a symptom of pulmonary fibrosis in said subject. Each possibility represents a separate embodiment. In another embodiment, said subject is diagnosed with severely impaired lung functions characterized by diffusing capacity (DLCO)<30% and/or forced vital capacity (FVC) <50%. In yet another embodiment, said subject is afflicted with IPF.

In other embodiments, the methods of the invention are used for inhibiting or preventing a symptom of fibrosis. In some embodiments, the methods of the present invention comprise at least one of inducing apoptosis and/or reducing the survival rate of fibroblast, myofibroblast cells or epithelial cells under epithelial-mesenchymal transition (EMT) in a tissue undergoing fibrosis, thereby treating a medical condition associated with fibrosis. In yet other embodiments, the methods of the present invention comprise regaining epithelial cells under EMT, fibroblast or myofibroblast cells susceptibility to immune system surveillance, thereby treating a medical condition associated with fibrosis. In a particular embodiment, said cells are lung fibroblasts, myofibroblasts or epithelial cells under EMT. Each possibility represents a separate embodiment of the invention. In another embodiment, the subject to be treated by the compositions and methods of the invention is human.

In another aspect, there is provided a method of inhibiting SIRT1-mediated signaling in a cell selected from the group consisting of a fibroblast, a myofibroblast, and an epithelial cell under EMT, the method comprising contacting the cell with an effective amount of a compound represented by the structure of Formula X as defined herein. In one embodiment, the contacting is performed in vitro. In another embodiment, the contacting is performed ex vivo. In another embodiment, the contacting is performed in vivo. In a particular embodiment, said cells are lung-derived cells, e.g. lung fibroblasts, lung myofibroblasts or lung epithelial cells under EMT, wherein each possibility represents a separate embodiment of the invention. In another embodiment, the method comprises inhibiting SIRT1-mediated deacetylation of Ku70. In another embodiment, the method comprises inhibiting SIRT1-mediated fibrotic activity. In another embodiment, the method comprises increasing SIRT1-mediated apoptosis. In another embodiment, the method comprises enhancing Fas signaling. In yet another embodiment, the method comprises inhibiting SIRT1-mediated signaling of additional pro-fibrotic cell populations characterized by FLIP overexpression, e.g. in reprogramming epithelial cells.

In another embodiment, there is provided a compound as disclosed herein, for use in treating or inhibiting fibrosis in a subject in need thereof, in the treatment of a fibrotic disorder, in the treatment of a condition associated with pulmonary fibrosis, or in inhibiting SIRT1-mediated signaling in a cell selected from the group consisting of fibroblast, myofibroblast and epithelial cell under EMT, wherein each possibility represents a separate embodiment of the invention.

According to yet another embodiment, the fibrosis is selected from the group consisting of pulmonary fibrosis, heart fibrosis, liver fibrosis, kidney fibrosis, and skin fibrosis. Each possibility represents a separate embodiment. In another embodiment, the fibrosis is associated with organ transplantation, chemotherapy, autoimmunity, surgery, irradiation, heart disease, liver cirrhosis, renal failure, keloid-skin fibrosis, idiopathic pulmonary fibrosis, and fibrosis associated with asthma. Each possibility represents a separate embodiment. According to yet another embodiment, the fibrosis is associated with idiopathic pulmonary fibrosis.

In some embodiments, the compounds of the invention downregulate deacetylase activity, specifically in IPF lung myofibroblasts. In some embodiments, the deacetylase activity is SIRT1-mediated. As disclosed herein, compounds in accordance with embodiments of the invention inhibit SIRT1-mediated deacetylation on non-histone substrates. In another embodiment, the compounds inhibit lysine residue deacetylation of SIRT1-protein substrates such as Ku70. In another embodiment, said compounds inhibit SIRT1 expression and/or activity in fibrotic-lung fibroblasts. In another embodiment, said compounds are capable of downregulating SIRT1-mediated signaling in fibroblasts from lungs of humans afflicted with IPF.

In another embodiment, the compounds are structural mimetics of an ε-N-acetylated lysine residue. In other embodiments, said compounds are capable of specifically competing with binding of ε-N-acetylated lysine residue to SIRT1. In another embodiment, said compounds are capable of competing with binding of Ku70 substrate to SIRT1. In yet another embodiment, said compounds are capable of specifically binding a molecular target (binding pocket) on SIRT1 protein comprising at least one of $Val^{412}$ (main chain)

and $His^{363}$ (side chain). In further embodiments, said molecular target further comprises a nicotinamide adenine dinucleotide ($NAD^+$) cofactor. In another embodiment, said compounds are capable of specifically binding SIRT1 and HDAC8 binding pockets.

In another embodiment, the deacetylase activity is mediated by SIRT1 and HDAC8. In another embodiment, said compounds inhibit deacetylase activity mediated by SIRT1 and HDAC8 to a greater extent than their inhibition of deacetylase activity mediated by HDACs other than SIRT1 and HDAC8. Hitherto known HDAC inhibitors, currently approved for the treatment of fibrosis-associated disorders, typically inhibit zinc-dependent HDAC (classes I, II and/or IV) without inhibiting Sirtuins, namely the structurally distinct NAD-dependent (class III) HDAC. In contradistinction, disclosed herein in embodiments of the invention are compounds inhibiting both class I and class III HDACs. In another embodiment, said compounds contain a hydroxamate moiety. While the involvement of hydroxamate moiety in binding zinc ions of zinc-dependent enzymes (e.g., HDAC classes I, II, and/or IV) has been suggested, it is now disclosed for the first time that compounds containing a hydroxamate moiety are also capable of binding to the active site of SIRT1 which lacks the zinc ions. Without being bound by any theory or mechanism of action, it is contemplated that this binding affinity to zinc-dependent HDAC and NAD-dependent HDAC enables the improved potency in the treatment of fibrosis, in particular IPF.

As disclosed herein, compounds according to embodiments of the invention exhibit anti-fibrotic properties. In some embodiments, the compounds enhance apoptosis in pro-fibrotic cells such as IPF lung myofibroblasts. In another embodiment, said apoptosis is Fas-mediated. In another embodiment, said apoptosis is FLIP-mediated (inhibited). In some embodiments, compounds useful in the context of the invention are effective anti-fibrotic agents despite their ability to induce only partial or limited FLIP downregulation. In other embodiments, the compounds are potent SIRT1 downregulators and moderate FLIP downregulators, e.g. retaining 20-80%, 30-70%, 40-60%, 20-40% or 30-50% of the FLIP expression levels measured in FLIP-overexpressing cells such as IPF lung myofibroblasts.

Further embodiments and the full scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

(FIG. 1A) FLIP (arrows) in BLM-treated murine lung tissue with fibrosis (day 1, 14) and at resolution (day 28, 56). Representative of 15 fields (×20) in each mouse. n=4. (FIG. 1B) Light microscopy images with trypan blue exclusion (inserted numbers), and (FIG. 1C) graphical presentation of control-IgG vs. Jo2 (20 μg, 48 h) anti-Fas monoclonal antibody (mAb)-treated fibroblasts from days 1, 14, 28, and 56 post BLM. *p=0.021.

(FIG. 2A) Flow cytometry of myofibroblasts from lungs resolving fibrosis (low FLIP), transfected with FLIP cDNA vector (cDNA-FLIP), compared to controls (cDNA-Ctl), and (FIG. 2C) fibrotic-lung myofibroblasts (high FLIP) transduced with shRNA-FLIP-$GFP^+$ lentiviral vector (shRNA-FLIP) vs. controls (shRNA-Ctl). (FIG. 2B, FIG. 2D) Flow cytometry of Annexin V staining and percent of apoptosis in cells transfected with cDNA or shRNA as described in FIGS. 2A and 2C, respectively, and treated with Jo2. n=4, *P<0.05. (FIG. 2E) FLIP in lung tissue sections and (FIG. 2F) Western blot (WB) with optical densities (OD) and ratios to β-actin of isolated lung fibroblasts. (FIG. 2G) Lung tissue section hematoxylin and eosin (H&E) staining, 14 days post oropharyngeal aspiration of BLM (OA-BLM) and 6 days after treatment with OA-CMV-GFP lentiviral-vector bearing shRNA-FLIP (shRNA-FLIP) or control (shRNA-Ctl).

FIG. 3A-3F. Increased SIRT1 with decreased Ku70 acetylation in human IPF-lung myofibroblasts and attenuated lung fibrosis with decreased FLIP in BLM-treated SIRT1y/y mice. SIRT1 immunoblot (IB) (FIG. 3A-B, upper panels) and Ku70 immunoprecipitation (IP) with subsequent pan-acetyl IB (FIG. 3A-B, lower panels) in fibroblasts isolated from IPF- vs. normal (NL) lungs (FIG. 3A), and saline (SAL)- vs. BLM-treated mice (FIG. 3B). SIRT1 (FIG. 3C, upper panels), FLIP (FIG. 3C, lower panels), (×20 and ×40 inserts), H&E (FIG. 3D, upper panels), and trichrome (FIG. 3D, lower panels) in lung tissue sections of SIRT1y/y vs. WT mice, 14 days post BLM. Graphical presentation of (FIG. 3E) semi-quantitative morphology index (SMI) of H&E staining, and (FIG. 3F) collagen Sircol assay. Representative of two experiments. n=4-5. *P<0.05.

(FIG. 4A) CMH docks into the SIRT1 narrow hydrophobic pocket with binding to the NAD cofactor, $Val^{412}$ ("V") and $His^{363}$ ("H"). (FIG. 4B) Crystallographic structure superimposition of CMH and SIRT1 substrate (Ku-70) shows high similarity to acetylated lysine. (FIG. 4C) CMH in the SIRT1 active site-binding pocket. WB of IP-Ku70 followed by (FIG. 4D) pan-acetyl mAb IB, or (FIG. 4E) anti-FLIP mAb of CMH (30 μM) vs. 4% DMSO (vehicle)-treated IPF-lung myofibroblast ATCC191 cell line ($3\times10^5$). (FIG. 4F) WB and, (FIG. 4G) flow cytometry analyses using anti-FLIP mAb. Representative of five experiments. n=4–5. *P<0.05.

(FIG. 5A) Light microscopy images with trypan blue exclusion (inserted numbers), and graphical representation (FIG. 5B), of IPF-lung myofibroblasts treated by anti-human Fas mAb (α-Fas) or control antibody (IgG). (FIG. 5C) WB showing caspase-3 (casp-3) cleavage of CMH vs. vehicle and Jo2 (20 μg, 48 h) anti-Fas mAb-treated IPF lung myofibroblasts (ATCC191 cell line). O.D ratios of cleaved to uncleaved caspase-3 are shown. Representative of four experiments.

(FIG. 6A) Schematic presentation of CMH administration into BLM-treated (0.05 mU) C57BL/6 WT mice. On day 6 after BLM, each mouse was further treated with 30 μM CMH or control 4% DMSO (vehicle) and sacrificed at day 14 post BLM. (FIG. 6B) IHC of lung SIRT1 and FLIP expression (×20 and ×40 inserts), marked by arrows in upper and lower panels, respectively. Lung-fibroblast Ku70-IP and IB of (FIG. 6C) SIRT1, (FIG. 6D) pan-acetyl, and (FIG. 6E) FLIP, are shown, and the O.D. ratios to the control protein GAPDH are indicated. (FIG. 6F) IHC of H&E and trichrome staining in lung tissue sections (upper and lower panels, respectively). (FIG. 6G) SMI grading lung pathology and (FIG. 6H) collagen Sircol assay. Representative of two experiments. n=5-6. *P<0.02.

(FIG. 7A) Pan-acetyl immunoblots of IPF-lung vs. normal-lung myofibroblasts (191 vs. 151, respectively). (FIG. 7B) Pan-acetyl immunoblots of IPF-lung myofibroblasts treated with CMH vs. vehicle. O.D. ratios to the control protein GAPDH are indicated.

(FIG. 8A) Pan-acetyl immunoblots of IPF-lung cells treated with a compound of Formula 6 (1 μM) vs. vehicle. (FIG. 8B) Immunoblots of Ku70 with anti-Ku70 mAb of IPF-lung treated with a compound of Formula 6 (1 μM) vs. vehicle. (FIG. 8C) Immunoblot of FLIP with anti-FLIP mAb of IPF-lung treated with a compound of Formula 6 (1 or 3 μM) vs. vehicle.

DETAILED DESCRIPTION OF THE INVENTION

Figure 1A:
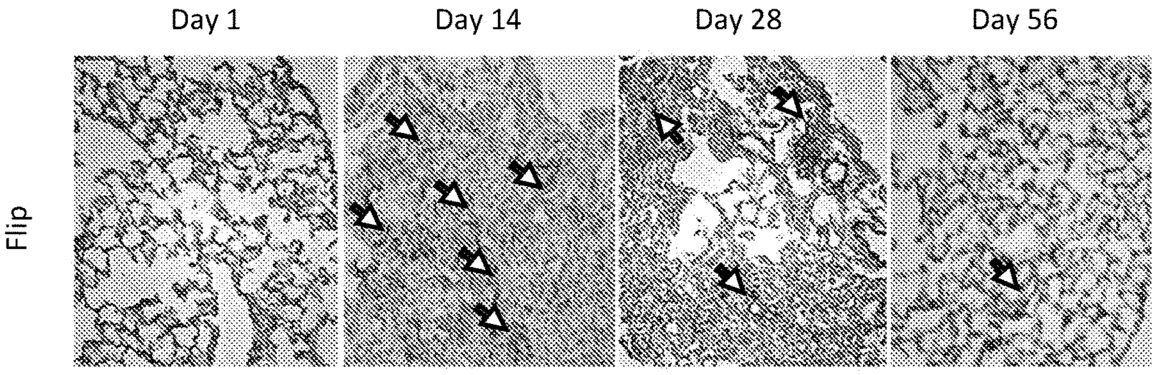
FIG. 1A-1C. Lung fibrosis resolution in mice correlates with loss of FLIP and myofibroblast apoptosis.

The present invention relates to compounds, compositions and methods for treating fibrosis. The present invention relates, in some embodiments, to compounds that inhibit or downregulate Sirtuin 1 (SIRT1) activity and their use in treating fibrosis, particularly IPF. The invention further relates to improved anti-fibrotic compounds characterized by advantageous properties.

To date, no efficient therapeutic approach for treating fibrotic conditions such as IPF exists. While certain drugs (e.g. nintedanib) have been shown to improve the quality of life of IPF patients, no improvement in their survival rate has been acknowledged. Thus, to date, lung transplantation still remains the most viable course of treatment to extend the lives of IPF patients.

Accordingly, there is an unmet need for highly potent anti-fibrotic agents exhibiting desirable pharmacokinetic properties including solubility and bioavailability. While 4-(4-Chloro-2-methylphenoxy)-N-hydroxybutanamide (CMH) has been shown to downregulate FLIP and attenuate lung fibrosis in an in-vivo model utilizing C57BL/6 mice lungs following bleomycin instillation, its pharmacokinetic properties including, but not limited to, low water solubility, compromise its use as an anti-fibrotic drug.

Disclosed herein in some embodiments are compounds that exhibit enhanced efficacy in the treatment and management of fibrosis, particularly pulmonary fibrosis, while exerting desirable pharmacokinetic properties.

According to certain aspects and embodiments, the present invention provides anti-fibrotic compounds that mimic ε-N-acetylated lysine residue and are capable of binding SIRT1 and HDAC8 with enhanced specificity.

The present invention is based, in part, on the unexpected discoveries that SIRT1 and Ku70-deacetylation are increased in IPF- as well as in bleomycin (BLM)-treated lung myofibroblasts; further, BLM-treated chimeric mice with deficient SIRT1, specifically in myofibroblasts, were found to downregulate FLIP and show less fibrosis. The invention is also based, in part, on the surprising identification of CMH, a modulator of FLIP-mediated signaling, as a previously unrecognized SIRT1 inhibitor. CMH was unexpectedly found to dock into a SIRT1 lysine binding-site and inhibit Ku70 deacetylation, destabilize the Ku70/FLIP complex and FLIP in IPF-lung myofibroblasts. CMH is further disclosed herein to alter apoptosis pathways regulated by SIRT1 and Ku70 in human IPF-lung myofibroblasts, and to inhibit lung myofibroblast SIRT1, Ku70-deacetylation, Ku70/FLIP complex, FLIP expression, and fibrosis evolution in BLM-treated mice.

The present invention thus provides anti-fibrotic agents, pharmaceutical compositions comprising same and use thereof in inhibiting SIRT1-mediated deacetylation of Ku70, inhibiting SIRT1-mediated fibrotic activity, increasing SIRT1-mediated apoptosis, enhancing Fas signaling, and inhibiting SIRT1-mediated signaling of additional pro-fibrotic cell populations characterized by FLIP overexpression, e.g. in reprogramming epithelial cells.

In one aspect, the invention relates to a compound represented by the structures and formulae as disclosed herein. In another aspect there is provided a pharmaceutical composition comprising a therapeutically effective amount of a compound represented by structures and formulae as disclosed herein, for use in treating or inhibiting fibrosis (including in particular pulmonary fibrosis) in a subject in need thereof. In another aspect there is provided a method of treating or inhibiting pulmonary fibrosis in a subject in need thereof, the method comprising administering to the subject a pharmaceutical composition comprising a therapeutically effective amount of a compound as disclosed herein. In yet another aspect, the invention relates to a method of treating a condition associated with pulmonary fibrosis in a subject in need thereof, the method comprising administering to the subject a composition comprising a therapeutically effective amount of a compound as defined herein, wherein the treatment comprises alleviating a symptom of pulmonary fibrosis in said subject. According to a further aspect, there is provided a method of inhibiting SIRT1-mediated signaling in a cell selected from the group consisting of fibroblast, myofibroblast and epithelial cell under epithelial-mesenchymal transition (EMT), the method comprising contacting the cell with an effective amount of a compound as disclosed herein.

Anti-Fibrotic Agents

According to certain aspects and embodiments, compounds useful in the context of the present invention are represented by the structure of Formula X:

Formula X

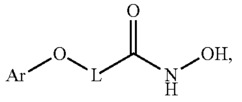

wherein L is a linker selected from the group consisting of $C_1$-$C_{10}$ alkylene, $C_2$-$C_{10}$ alkenylene, $C_2$-$C_{10}$ alkynylene, $C_1$-$C_9$ heteroalkylene, $C_1$-$C_9$ heteroalkenylene, $C_1$-$C_9$ heteroalkynylene, $C_3$-$C_{10}$ cycloalkylene, $C_1$-$C_9$ heterocycloalkylene, $C_6$-$C_{24}$ arylene, $C_5$-$C_{23}$ heteroarylene; and Ar is selected from the group consisting of $C_6$-$C_{18}$ aryl and $C_5$-$C_{17}$ heteroaryl. Each possibility represents a separate embodiment.

Within the scope of the present invention are substitutions of each of L and Ar, independently, with at least one of hydroxy, halogen, haloalkyl, $C_1$-$C_4$ alkyl, $C_1$-$C_4$ alkoxy, $C_6$-$C_{10}$ aryl, amido, alkylamido, amino, alkylamino, carboxyl, $CH_2CH_2OH$, $CH_2CH_2OCH_2CH_2OH$, cyano, and nitro. Each possibility represents a separate embodiment. In one embodiment, the compound of Formula X is not 4-(4-Chloro-2-methylphenoxy)-N-hydroxybutanamide (CMH). In another embodiment, the compound of Formula X is not 7-(4-(3-ethynylphenylamino)-7-methoxyquinazolin-6-yloxy)-N-hydroxyheptanamide (CUDC-101).

The present invention further provides compounds represented by the structure of Formula X comprising any one or more of the following substitutions:

1. L is $C_1$-$C_{10}$ alkylene, $C_2$-$C_{10}$ alkenylene, or $C_2$-$C_{10}$ alkynylene, optionally further substituted with at least one of hydroxy, halogen, haloalkyl, $C_1$-$C_4$ alkyl, $C_1$-$C_4$ alkoxy, $C_6$-$C_{10}$ aryl, amido, alkylamido, amino, alkylamino, carboxyl, $CH_2CH_2OH$, $CH_2CH_2OCH_2CH_2OH$, cyano, and nitro. Each possibility represents a separate embodiment.
2. L is a $C_1$-$C_{10}$ alkylene.
3. L is a $C_2$-$C_6$ alkylene.
4. L is a $C_2$-$C_4$ alkylene.
5. L is a $C_2$-$C_5$ alkylene.
6. L is a $C_4$-$C_6$ alkylene.
7. L is a $C_4$-$C_5$ alkylene.
8. Ar is a phenyl substituted with at least one of methyl, methoxy, amido, amino, and nitro.
9. Ar is a phenyl substituted with one of methyl, methoxy, amido, amino, and nitro.
10. Ar is a phenyl substituted with one of methyl, methoxy, amido, amino, and nitro in the para position.
11. Ar is a $C_{10}$-$C_{18}$ fused bicyclic aryl optionally substituted with at least one of hydroxy, amido, alkylamido, amino, alkylamino, carboxyl, $CH_2CH_2OH$, and $CH_2CH_2OCH_2CH_2OH$.
12. Ar is a $C_5$-$C_9$ fused bicyclic heteroaryl optionally substituted with at least one of hydroxy, amido, alkylamido, amino, alkylamino, carboxyl, $C_1$-$C_4$ alkyl, $C_1$-$C_4$ alkoxy, halogen, haloalkyl, nitro, cyano, $CH_2CH_2OH$, and $CH_2CH_2OCH_2CH_2OH$, provided that when Ar is substituted with methoxy and amino, then the amino is not an aniline.
13. L is a $C_2$-$C_6$ alkylene, and Ar is a $C_5$-$C_9$ fused bicyclic heteroaryl optionally substituted with at least one of hydroxy, amido, alkylamido, amino, alkylamino, carboxyl, $C_1$-$C_4$ alkyl, $C_1$-$C_4$ alkoxy, halogen, haloalkyl, nitro, cyano, $CH_2CH_2OH$, and $CH_2CH_2OCH_2CH_2OH$, provided that when Ar is substituted with methoxy and amino, then the amino is not an aniline group.
14. L is a $C_2$-$C_6$ alkylene, and Ar is a $C_5$-$C_9$ fused bicyclic heteroaryl optionally substituted with at least one of hydroxy, amido, alkylamido, amino, alkylamino, carboxyl, $C_1$-$C_4$ alkyl, $C_1$-$C_4$ alkoxy, nitro, cyano, $CH_2CH_2OH$, and $CH_2CH_2OCH_2CH_2OH$, provided that when Ar is substituted with methoxy and amino, then the amino is not an aniline group.
15. L is a $C_2$-$C_6$ alkylene, and Ar is a $C_5$-$C_9$ fused bicyclic heteroaryl optionally substituted with at least one of methoxy, amino and amido, provided that when Ar is substituted with methoxy and amino, then the amino is not an aniline group.
16. L is a $C_2$-$C_6$ alkylene and Ar is $C_{10}$-$C_{18}$ fused bicyclic aryl.
17. L is a $C_2$-$C_5$ alkylene and Ar is a naphthyl.
18. L is a $C_4$-$C_5$ alkylene and Ar is a naphthyl.
19. L is a $C_4$ alkylene and Ar is a phenyl substituted with at least one of methyl, methoxy, amido, amino, and nitro.
20. L is a $C_4$ alkylene and Ar is a phenyl substituted with one of methyl, methoxy, amido, amino, and nitro.
21. L is a $C_4$ alkylene and Ar is a phenyl substituted with one of methyl, methoxy, amido, amino, and nitro in para position.
22. L is a $C_4$ alkylene and Ar is a phenyl substituted with at least one of methyl, amido, amino, and nitro.
23. L is a $C_4$ alkylene and Ar is a phenyl substituted with one of methyl, amido, amino, and nitro.
24. L is a $C_4$ alkylene and Ar is a phenyl substituted with one of methyl, amido, amino, and nitro in para position.
25. L is a $C_6$ alkylene and Ar is a phenyl substituted with methoxy.
26. L is a $C_6$ alkylene and Ar is a phenyl substituted with methoxy in para position.
27. L is a $C_4$ alkylene and Ar is tolyl.
28. L is a $C_4$ alkylene and Ar is phenyl substituted with nitro, amino, or amido.
29. L is a $C_4$ alkylene and Ar is phenyl substituted with nitro, amino, or amido in para position.
30. L is a $C_2$-$C_4$ alkylene and Ar is $C_5$-$C_9$ fused bicyclic heteroaryl substituted with at least one of methoxy, amido, and amino, provided that when Ar is substituted with methoxy and amino, then the amino is not an aniline group.

Representative and non-limiting examples of such structures are compounds selected from the group consisting of compounds of Formulae 1-18, with each possibility representing a separate embodiment. In certain aspects and embodiments, the compound is represented by the structure of any one of Formulae 1, 3, 4, 5, 6, 7, 8, 9, 10, 11, 12, 13, 14, 15, 16, 17, and 18. Each possibility represents a separate embodiment. In other aspects and embodiments, the compound is represented by the structure of any one of Formulae 1, 2, 3, 4, 5, 6, 7, 8, 9, 10, 12, 13, 14, 15, 16, 17, and 18. Each possibility represents a separate embodiment. In one embodiment, the compound represented by the structure of Formula X is a compound of Formula 6 or 12. Each possibility represents a separate embodiment. In other embodiments, the compound represented by the structure of Formula X is a compound of any one of Formula 1 to 5; a compound of any one of Formula 6 to 12; or a compound of any one of Formula 13 to 18, with each possibility representing a separate embodiment.

The present invention is further directed to novel highly potent anti-fibrotic compounds that are structural mimetics of an ε-N-acetylated lysine residue. Within the scope of the present invention are compounds represented by the structure of Formula X:

Formula X

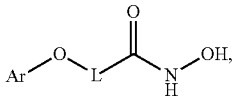

wherein L is a $C_2$-$C_6$ alkylene, and Ar is a $C_5$-$C_9$ fused bicyclic heteroaryl optionally substituted with at least one of hydroxy, amido, alkylamido, amino, alkylamino, carboxyl, $C_1$-$C_4$ alkyl, $C_1$-$C_4$ alkoxy, nitro, $CH_2CH_2OH$, and $CH_2CH_2OCH_2CH_2OH$, provided that when Ar is substituted with methoxy and amino, then the amino is not an aniline group.

Further provided are compounds represented by the structure of Formula X, wherein L is a $C_2$-$C_6$ alkylene, and Ar is a $C_5$-$C_9$ fused bicyclic heteroaryl optionally substituted with at least one of methoxy, amino and amido, provided that when Ar is substituted with methoxy and amino, then the amino is not an aniline group. Additional compounds within the scope of the present invention are those represented by the structure of Formula X, wherein L is a $C_4$ alkylene, and Ar is phenyl substituted with at least one of methyl, amido, amino, and nitro. Each possibility represents a separate embodiment. In particular embodiments, the compounds represented by the structure of Formula X in which Ar is phenyl are substituted with one substituent selected from methyl, amido, amino, and nitro, preferably in para position. Each possibility represents a separate embodiment.

Representative and non-limiting examples of such structures are compounds selected from the group consisting of compounds of Formulae 1-5, and 13-18, with each possibility representing a separate embodiment. In several aspects and embodiments, the compounds are represented by the structure of any one of Formulae 13-18, with each possibility representing a separate embodiment. In one embodiment, the compound is represented by the structure of Formula 15.

The term "alkyl" as used herein refers to any saturated aliphatic hydrocarbon, including straight-chain and branched-chain alkyl groups. In one embodiment, the alkyl group has 1-10 carbons designated herein as $C_1$-$C_{10}$ alkyl. In another embodiment, the alkyl group has 1-4 carbons designated herein as $C_1$-$C_4$ alkyl (e.g., methyl, ethyl, propyl, isopropyl, n-butyl, sec-butyl and t-butyl). The term "heteroalkyl" as used herein refers to an "alkyl" group in which at least one carbon atom has been replaced with a heteroatom (e.g., an O, N, or S atom). In one embodiment, the heteroalkyl does not contain an S atom.

The term "alkenyl" as used herein refers to an aliphatic hydrocarbon group containing at least one carbon-carbon double bond including straight-chain and branched-chain alkenyl groups. In one embodiment, the alkenyl group has 2-10 carbon atoms designated herein as $C_2$-$C_{10}$ alkenyl (e.g. ethenyl, propenyl, n-butenyl, i-butenyl, 3-methylbut-2-enyl, n-pentenyl, heptenyl, octenyl, cyclohexyl-butenyl and decenyl). The term "heteroalkenyl" as used herein refers to an "alkenyl" group in which at least one carbon atom has been replaced with a heteroatom (e.g., an O, N, or S atom). In one embodiment, the heteroalkenyl does not contain an S atom.

The term "alkynyl" as used herein refers to an aliphatic hydrocarbon group containing at least one carbon-carbon triple bond including straight-chain and branched-chain. In one embodiment, the alkynyl group has 2-10 carbon atoms designated herein as $C_2$-$C_{10}$ alkynyl (e.g. ethynyl, propynyl, n-butynyl, 2-butynyl, 3-methylbutynyl, n-pentynyl, heptynyl, octynyl and decynyl). The term "heteroalkynyl" as used herein refers to an "alkynyl" group in which at least one carbon atom has been replaced with a heteroatom (e.g., an O, N, or S atom). In one embodiment, the heteroalkynyl does not contain an S atom.

The term "cycloalkyl" as used herein refers to any saturated monocyclic or polycyclic group. In one embodiment, the cycloalkyl group has 3-10 carbon atoms designated herein as $C_3$-$C_{10}$ cycloalkyl (e.g. cyclopropyl, cyclobutyl, cyclopentyl, cyclohexyl, and cycloheptyl). The term "heterocycloalkyl" as used herein refers to a "cycloalkyl" group in which at least one carbon atom has been replaced with a heteroatom (e.g., an O, N, or S atom). In one embodiment, the heterocycloalkyl does not contain an S atom.

The term "aryl" as used herein refers to an aromatic ring system. In one embodiment, the aryl group has 6-24 ring carbon atoms designated herein as $C_6$-$C_{24}$ aryl. The aryl ring can be a monocyclic, bicyclic, tricyclic and the like. Non-limiting examples of aryl groups are phenyl, naphthyl including 1-naphthyl and 2-naphthyl, and the like. The term "heteroaryl" as used herein refers to an "aryl" group in which at least one carbon atom has been replaced with a heteroatom (e.g., an O, N, or S atom). In one embodiment, the heteroaryl does not contain an S atom. The heteroaryl contains 5 or more ring atoms. The heteroaryl group can be monocyclic, bicyclic, tricyclic and the like. Also included in this definition are the benzoheterocyclic rings. If nitrogen is a ring atom, the present invention also contemplates the N-oxides of the nitrogen containing heteroaryls. Non-limiting examples of heteroaryls include furyl, benzofuryl, pyrrolyl, imidazolyl, pyrazolyl, pyridyl, pyrazinyl, pyrimidinyl, pyridazinyl, indolyl, isoindolyl, indazolyl, purinyl, isoquinolyl, quinolyl, naphthyridinyl, quinoxalinyl, quinazolinyl, cinnolinyl, pteridinyl, carbolinyl, oxazolyl, isoxazolyl and the like.

It is to be understood that the designated number of carbons in heteroforms of heteroalkyl, heteroalkenyl heteroalkynyl, heterocycloalkyl, and heteroaryl does not include the heteroatom count. For example, if heteroalkyl is defined as $C_1$-$C_9$ heteroalkyl, it will contain 1-9 carbons in its backbone and in addition at least one heteroatom, for example N. Thus, for example, the compound $CH_2CH_2OCH_2CH_2$ is designated herein as a $C_4$ heteroalkyl.

As used herein, affixing the suffix "-ene" to a group indicates that the group is a divalent moiety, e.g., alkylene is the divalent moiety of alkyl, alkenylene is the divalent moiety of alkenyl, and so forth.

A "hydroxy" group refers to an OH group. An "alkoxy" group refers to an —O-alkyl group wherein R is alkyl as defined above.

An "amino" group refers to an $NH_2$ group. An alkylamino group refers to an —NHR group wherein R is alkyl is as defined above. A dialkylamino group refers to an —NRR' group wherein each R and R' individually at each occurrence is alkyl as defined above.

An "amido" group refers to a —C(O)$NH_2$ or an —NHC(O)R group. An alkylamido group refers to a —C(O)NHR or an —NHC(O)R group wherein R is alkyl as defined above. A dialkylamido group refers to an —C(O)NRR' group wherein each of R and R' individually at each occurrence is alkyl as defined above.

A "carboxyl" group refers to a —C(O)OH group or the corresponding base.

The term "halogen" or "halo" as used herein refers to chlorine, bromine, fluorine, and iodine. The term "haloalkyl" refers to an alkyl group as defined herein having some or all of the hydrogens independently replaced by a halogen group including, but not limited to, trichloromethyl, tribromomethyl, trifluoromethyl, triiodomethyl, difluoromethyl, chlorodifluoromethyl, pentafluoroethyl, 1,1-difluoroethyl, bromomethyl, chloromethyl, fluoromethyl, iodomethyl, and the like.

All stereoisomers of the compounds of the present invention are contemplated, either in admixture or in pure or substantially pure form. These compounds can have asymmetric centers at any of the atoms. Consequently, the compounds can exist in enantiomeric or diastereomeric forms or in mixtures thereof. The present invention contemplates the use of any racemates (i.e. mixtures containing equal amounts of each enantiomers), enantiomerically enriched mixtures (i.e., mixtures enriched for one enantiomer), pure enantiomers or diastereomers, or any mixtures thereof. The chiral centers can be designated as R or S or R,S or d,D,l,L or d,l, D,L. In addition, several of the compounds of the present invention contain one or more double bonds. The present invention intends to encompass all structural and geometrical isomers including cis, trans, E and Z isomers and optical isomers, independently at each occurrence.

One or more of the compounds of the invention, may be present as a salt. The term "salt" encompasses both basic and acid addition salts. Suitable base addition salts include, but are not limited to, metallic salts of calcium, lithium, magnesium, potassium, sodium, aluminum, ferric and zinc; ammonium salts derived from ammonia, primary, secondary, tertiary and quaternary amines, non-limiting examples of which are trimethylamine, cyclohexylamine, benzylamine, dibenzylamine, 2-hydroxyethylamine, bis(2-hydroxyethyl) amine, phenylethylbenzylamine, dibenzylethylenediamine, procaine, chloroprocaine, piperidine, monoethanolamine, triethanolamine, quinine, choline, N-methylglucosamine. Each possibility represents a separate embodiment. Suitable acid addition salts include salts derived from inorganic acids such as, but not limited to, hydrochloric, nitric, phosphoric, sulfuric, hydrobromic, hydriodic, phosphorous, and the like, as well as salts derived from organic acids such as aliphatic mono- and dicarboxylic acids such as acetic acid or oxalic acid, phenyl-substituted alkanoic acids, hydroxy alkanoic acids, alkanedioic acids, aromatic acids, aliphatic and aromatic sulfonic acids and the like. Each possibility represents a separate embodiment. The salts thus include sulfate, pyrosulfate, bisulfate, sulfite, bisulfite, nitrate, phosphate, monohydrogenphosphate, dihydrogenphosphate, metaphosphate, pyrophosphate, chloride, bromide, iodide, acetate, propionate, caprylate, isobutyrate, oxalate, malonate, succinate, suberate, sebacate, fumarate, maleate, mandelate, benzoate, chlorobenzoate, methylbenzoate, dinitrobenzoate, phthalate, benzenesulfonate, toluenesulfonate, phenylacetate, citrate, lactate, maleate, tartrate, methanesulfonate, and the like. Each possibility represents a separate embodiment.

The base addition salts may be prepared by known methods of the art in which the free acid form is brought into contact with a sufficient amount of the desired base to produce the salt. Likewise, the acid addition salts may be prepared by known methods of the art in which the free base form is brought into contact with a sufficient amount of the desired acid to produce the salt.

According to the principles provided herein, solvates of any of compounds represented by the structure of Formula X or any of the compounds represented by the structure of Formulae 1-18 and salts thereof are included within the scope of the present invention. As used herein, the term "solvate" refers a physical association of a compound of the invention with one or more solvent molecules. This physical association involves varying degrees of ionic and covalent bonding, including hydrogen bonding. In certain instances, the solvate will be capable of isolation. "Solvate" encompasses both solution-phase and isolatable solvates. Non-limiting examples of suitable solvates include ethanolates, methanolates and the like. "Hydrate" is a solvate wherein the solvent molecule is water.

The present invention also includes polymorphs of any of compounds represented by the structure of Formula X or any of compounds represented by the structure of Formulae 1-18 and salts thereof. The term "polymorph" refers to a particular crystalline state of a substance, which can be characterized by particular physical properties such as X-ray diffraction, IR spectra, melting point, and the like.

In particular, compounds useful for the compositions and methods according to embodiments of the invention are disclosed herein to downregulate deacetylase activity, in particular in IPF lung myofibroblasts. In some embodiments, the deacetylase activity is associated with a histone deacetylase (HDAC). In other embodiments, the compounds inhibit deacetylation on non-histone HDAC targets (substrates). In a particular embodiment, the compounds inhibit Ku70 deacetylation. In another embodiment, the compounds inhibit histone deacetylation. In another embodiment, the compounds inhibit deacetylation of both non-histone targets (such as Ku70) and histone targets.

In various embodiments, the inhibition or downregulation may be by at least 10%, 20%, 30%, 40%, 50%, 60%, 70%, 80% or 90%, and up to 100%, e.g. by 20-80%, 30-70%, 40-60%, 20-40% or 30-50%, wherein each possibility represents a separate embodiment of the invention. For example, potent inhibitors may inhibit or downregulate more than 50% of the activity, whereas moderate inhibitors may inhibit or downregulate up to 30-50% of the activity. In some embodiments, the downregulation of SIRT1-mediated deacetylase activity measured is manifested by at least twofold and typically by at least 10- , 20-, 40-, 60- or 80-fold enhancement in Ku-70 acetylation compared to its acetylation level prior to treatment. In a particular embodiment, said inhibition is associated with enhanced Ku-70 acetylation by about 80-fold and downregulated FLIP expression by about twofold, e.g. in human IPF-lung myofibroblasts.

In another embodiment, the deacetylase activity is SIRT1-mediated (namely exerted by a SIRT1 enzyme on a corresponding substrate). As disclosed herein, compounds in accordance with embodiments of the invention inhibit SIRT1-mediated deacetylation on non-histone substrates. In another embodiment, the compounds inhibit lysine residue deacetylation of SIRT1-protein substrates such as Ku70. In another embodiment, said compounds inhibit SIRT1 expression and/or activity in fibrotic-lung fibroblasts. In another embodiment, said compounds are capable of downregulating SIRT1 signaling in fibroblasts from lungs of humans with IPF. In another embodiment, said compounds are capable of mimicking an ε-N-acetylated lysine residue. In another embodiment, said compounds are capable of competing with binding of Ku70 substrate to SIRT1 or of specifically binding a molecular target (binding pocket) on SIRT1 which comprises the binding to at least one of $Val^{412}$ (main chain) and/or $His^{363}$ (side chain), with each possibility representing a separate embodiment. In further embodiments, said binding further comprises binding to an NAD cofactor.

As used herein, the terms "mimetic" or "capable of mimicking" an ε-N-acetylated lysine residue, refer to a compound that is structurally similar in terms of size (e.g. molecular weight, length etc.), configuration, and/or electrostatic potential, to an ε-N-acetylated lysine residue, so as to enable binding to a molecular target thereof, for example the binding pocket on SIRT1. Binding to the pocket of SIRT1 typically involves at least one of the following non-covalent interactions including, but not limited to, hydrogen bonding, π-interactions, van der Waals interactions, hydrophobic interactions, hydrophilic interactions, and electrostatic interactions. In some embodiments, binding involves at least one of the amino acid residues of SIRT1 selected from $Val^{412}$ (main chain) and $His^{363}$ (side chain). In certain embodiments, binding of the compound of the present invention to SIRT1 comprises high affinity binding such that it competes with binding of Ku70 substrate to SIRT1. Exemplary methods and in silico resources for determining structure and function (e.g. binding) parameters are provided in the Examples section herein.

In another embodiment, the deacetylase activity is HDAC8-mediated. In another embodiment, the deacetylase activity is mediated by SIRT1 and HDAC8. In another embodiment, said compounds inhibit deacetylase activity mediated by SIRT1 and HDAC8 to a greater extent than other HDACs. Hitherto known HDAC inhibitors, currently approved for the treatment of fibrosis-associated disorders, typically inhibit zinc-dependent HDAC (classes I, II and/or IV) without inhibiting Sirtuins, namely the structurally distinct NAD-dependent (class III) HDAC. In contradistinction, disclosed herein in embodiments of the invention are dual inhibitors, namely compounds inhibiting both class I and class III HDAC. In another embodiment, said compounds contain a hydroxamate moiety.

For example, without limitation, compounds in accordance with the invention may inhibit SIRT1 and/or HDAC8 activity by at least two-, three-, four-, five-, or ten-fold, or, in other embodiments, by at least 20, 40, 60 or 100-fold over their ability to inhibit other HDACs. In some embodiments, the compounds of the invention are selective to an HDAC (e.g. SIRT1 and/or HDAC8) enzyme as disclosed herein, and do not substantially inhibit other, non-related enzymes, such as lipoxygenases or cyclooxygenases. In a particular embodiment, said compounds are substantially devoid of lipoxygenase- and cyclooxygenase-inhibiting properties. In another particular embodiment, said compounds are selective to SIRT1 and/or HDAC8, and do not substantially inhibit other HDACs. In other embodiments, said compounds do not substantially inhibit class II HDACs and/or class IV HDACs. In another embodiment said compounds do not substantially inhibit HDAC1, HDAC2 and/or HDAC3. Each possibility represents a separate embodiment of the invention.

As disclosed herein, compounds according to embodiments of the invention exhibit anti-fibrotic properties. In some embodiments, the compounds enhance apoptosis in pro-fibrotic (fibrogenic) cells such as IPF lung myofibroblasts. In another embodiment, said apoptosis is Fas-mediated. In another embodiment, said apoptosis is FLIP-mediated. In some embodiments, compounds useful in the context of the invention are effective anti-fibrotic agents despite exhibiting partial or limited FLIP downregulation. In some embodiments, the compounds are potent SIRT1 inhibitors and moderate FLIP downregulates. In another embodiment, said compounds are capable of reducing FLIP levels in cells characterized by FLIP overexpression (e.g. IPF lung myofibroblasts) to a level characteristic of, or not substantially lower than in, the corresponding normal non-fibrotic cells.

For example, FLIP-overexpressing cells (e.g. pro-fibrotic cells such as IPF lung myofibroblasts) are typically characterized by 1.5-2.5-fold upregulation of cellular FLIP levels compared to the corresponding normal cells. In various embodiments, the compounds may retain 20-80%, 30-70%, 40-60%, 20-40%, 50-80% or 30-50% of the FLIP expression levels measured in these cells under physiological conditions, including each value within the specified ranges. In a particular embodiment, said compounds retain 40-60% of the FLIP expression levels in FLIP-overexpressing cells such as IPF lung myofibroblasts, including each value within the specified range.

Apoptosis or programmed cell death (PCD) is a form of cell death which is essential for the maintenance of homeostasis in multicellular organisms. Apoptosis can be induced by various stimuli and mediated by several pathways, including intrinsic and extrinsic apoptotic pathways. One such pathway involves Fas-mediated signaling, in which the tumor necrosis factor (TNF) receptor superfamily member Fas (CD95/Apo-1) serves a key function in the recognition and transduction of apoptotic signals through the extrinsic apoptosis pathway. Fas ligand (FasL) binding to aggregated transmembrane Fas trimers promotes the assembly of the death-inducing signaling complex (DISC) and the downstream activation of the caspase cascade required for the execution phase of apoptosis (characterized by cleavage of various cellular substrates and DNA fragmentation). PCD resulting from this signaling cascade and involving Fas/FasL is herein referred to as Fas-mediated (or Fas-induced) apoptosis.

Fibrogenic cells are often characterized by resistance to extrinsic apoptotic signals and thus remain and accumulate in the affected tissue, propagating fibrotic damage. For example, IPF fibroblasts and other pro-fibrotic fibroblasts may be resistant to Fas-mediated apoptosis due to overexpression or dysregulation of FLIP that may divert Fas signaling from apoptosis to proliferation. PCD inhibited or attenuated by FLIP is herein referred to as FLIP-mediated apoptosis.

In other embodiments, the invention relates to CMH analogs having improved properties. In various embodiments, said compounds exhibit enhanced efficacy, safety and/or bioavailability compared to known compounds such as CMH. In other embodiments, the improved properties include improved water solubility. In some embodiments, the improved properties comprise enhanced efficacy manifested by downregulation of SIRT1-mediated deacetylase activity, e.g. by 10-400-fold and typically 30-300-fold. For example, as demonstrated herein, compounds in accordance with embodiments of the invention exhibit enhanced Ku-70 acetylation of about 10 to 100-fold and typically 20 to 80-fold, e.g. about 40-fold over that exhibited by CMH, manifested by the level of acetylated Ku-70 in human IPF-lung myofibroblasts (measurable e.g. by immunoblotting or other suitable immunoassays). Additionally, as exemplified herein, the enhanced activity may be manifested by an effective concentration (e.g. evaluated as ED50) reduced by about 30-300-fold compared to CMH, which is required for exerting a beneficial biological activity as disclosed herein (e.g. downregulation of SIRT1-mediated deacetylase activity in human IPF-lung myofibroblasts).

Pharmaceutical Compositions

According to certain aspects and embodiments, the invention relates to a pharmaceutical composition comprising a therapeutically effective amount of a compound of Formulae X or 1-18 including salts, hydrates, solvates, polymorphs, optical isomers, geometrical isomers, enantiomers, diastereomers, and mixtures thereof, the pharmaceutical composition further comprising a pharmaceutically acceptable carrier or excipient. In a particular embodiment, the pharmaceutical composition comprises the compound disclosed herein as the sole active ingredient.

Suitable pharmaceutically acceptable carriers or excipients include, but are not limited to, a binder, a filler, a diluent, a surfactant or emulsifier, a glidant or lubricant, buffering or pH adjusting agent, a tonicity enhancing agent, a wetting agent, a preservative, an antioxidant, a flavoring agent, a colorant, and a mixture or combination thereof. Each possibility represents a separate embodiment.

Suitable binders include, but are not limited to, polyvinylpyrrolidone, copovidone, hydroxypropyl methylcellulose, starch, and gelatin. Each possibility represents a separate embodiment.

Suitable fillers include, but are not limited to, sugars such as lactose, sucrose, mannitol or sorbitol and derivatives therefore (e.g. amino sugars), ethylcellulose, microcrystalline cellulose, and silicified microcrystalline cellulose. Each possibility represents a separate embodiment.

Suitable lubricants include, but are not limited to, sodium stearyl fumarate, stearic acid, polyethylene glycol or stearates, such as magnesium stearate. Each possibility represents a separate embodiment.

Suitable diluents include, but are not limited to, dicalcium phosphate dihydrate, sugars, lactose, calcium phosphate, cellulose, kaolin, mannitol, sodium chloride, and dry starch. Each possibility represents a separate embodiment.

Suitable surfactants or emulsifiers include, but are not limited to, polyvinyl alcohol (PVA), polysorbate, polyethylene glycols, polyoxyethylene-polyoxypropylene block copolymers known as "poloxamer", polyglycerin fatty acid esters such as decaglyceryl monolaurate and decaglyceryl monomyristate, sorbitan fatty acid ester such as sorbitan monostearate, polyoxyethylene sorbitan fatty acid ester such as polyoxyethylene sorbitan monooleate (Tween), polyethylene glycol fatty acid ester such as polyoxyethylene monostearate, polyoxyethylene alkyl ether such as polyoxyethylene lauryl ether, polyoxyethylene castor oil and hardened castor oil such as polyoxyethylene hardened castor oil. Each possibility represents a separate embodiment.

Suitable glidants or lubricants include, but are not limited to, colloidal silicon dioxide, magnesium stearate, talc, and mineral oil. Each possibility represents a separate embodiment.

Suitable buffering or pH adjusting agents include, but are not limited to, acidic buffering agents such as short chain fatty acids, citric acid, acetic acid, hydrochloric acid, sulfuric acid and fumaric acid; and basic buffering agents such as tris, sodium carbonate, sodium bicarbonate, sodium hydroxide, potassium hydroxide, and magnesium hydroxide. Each possibility represents a separate embodiment.

Suitable tonicity enhancing agents include, but are not limited to, ionic and non-ionic agents such as, alkali metal or alkaline earth metal halides, urea, glycerol, sorbitol, mannitol, propylene glycol, and dextrose. Each possibility represents a separate embodiment.

Suitable wetting agents include, but are not limited to, glycerin, cetyl alcohol, and glycerol monostearate. Each possibility represents a separate embodiment.

Suitable preservatives include, but are not limited to, benzalkonium chloride, benzoxonium chloride, thiomersal, phenylmercuric nitrate, phenylmercuric acetate, phenylmercuric borate, methylparaben, propylparaben, chlorobutanol, benzyl alcohol, phenyl alcohol, chlorohexidine, and polyhexamethylene biguanide. Each possibility represents a separate embodiment.

Suitable antioxidants include, but are not limited to, sorbic acid, ascorbic acid, ascorbate, glycine, α-tocopherol, butylated hydroxyanisole (BHA), and butylated hydroxytoluene (BHT). Each possibility represents a separate embodiment.

Suitable flavoring agents include, but are not limited to, sweeteners such as sucralose and synthetic flavor oils and flavoring aromatics, natural oils, extracts from plants, leaves, flowers, and fruits, and combinations thereof. Exemplary flavoring agents include cinnamon oils, oil of wintergreen, peppermint oils, clover oil, hay oil, anise oil, eucalyptus, vanilla, citrus oil such as lemon oil, orange oil, grape and grapefruit oil, and fruit essences including apple, peach, pear, strawberry, raspberry, cherry, plum, pineapple, and apricot. Each possibility represents a separate embodiment.

Suitable colorants include, but are not limited to, alumina (dried aluminum hydroxide), annatto extract, calcium carbonate, canthaxanthin, caramel, β-carotene, cochineal extract, carmine, potassium sodium copper chlorophyllin (chlorophyllin-copper complex), dihydroxyacetone, bismuth oxychloride, synthetic iron oxide, ferric ammonium ferrocyanide, ferric ferrocyanide, chromium hydroxide green, chromium oxide greens, guanine, mica-based pearlescent pigments, pyrophyllite, mica, dentifrices, talc, titanium dioxide, aluminum powder, bronze powder, copper powder, and zinc oxide. Each possibility represents a separate embodiment.

In certain aspects and embodiment, the pharmaceutical composition of the present invention is formulated as tablet, pill, capsule (e.g. soft or hard gelatin capsule), pellets, granules, powder, a wafer, coated or uncoated beads, lozenge, sachet, cachet, elixir, an osmotic pump, a depot system, an iontophoretic system, a patch, suspension, dispersion, emulsion, solution, syrup, aerosol, oil, ointment, suppository, a gel, and a cream. Each possibility represents a separate embodiment.

For preparing solid compositions such as tablets, the active pharmaceutical ingredient is mixed with a pharmaceutical carrier or excipient to form a solid pre-formulation composition containing a substantially homogeneous distribution of the compound of the present invention in the pharmaceutical carrier or excipient.

Any method can be used to prepare the pharmaceutical compositions. For example, solid dosage forms can be prepared by wet granulation, dry granulation, direct compression and the like as is known in the art. The liquid forms in which the compounds of the present invention may be incorporated, for administration via a route selected from oral, topical or by injection, include aqueous solutions, suitably flavored syrups, aqueous or oil suspensions, and flavored emulsions with edible oils such as cottonseed oil, sesame oil, coconut oil, or peanut oil, as well as elixirs and similar pharmaceutical vehicles. Each possibility represents a separate embodiment.

The compositions of the present invention may be formulated as single-phase aqueous emulsion or multiple emulsions. According to some embodiments, the composition is formulated as an emulsion. These emulsions may be oil-in-water (o/w) emulsions, water-in-oil (w/o) emulsions, or multiple emulsions such as oil-in-water-in-oil (o/w/o) or water-in-oil-in-water (w/o/w) emulsions. It is understood that the oil phase can comprise silicone oils, non-silicone organic oils, or mixtures thereof. The compositions can comprise two immiscible phases that are reconstituted prior to use. Each possibility represents a separate embodiment of the present invention.

In certain embodiments, the compositions of the present invention are liposomal compositions comprising a compound represented by the structure of Formula X or any of Formulae 1-18 as defined herein encapsulated in a liposome comprising a lipid bilayer structure.

Another formulation employed in the methods of the present invention comprises transdermal delivery devices ("patches"). Such transdermal patches may be used to provide continuous or discontinuous infusion of the compound of the present invention in controlled amounts. The construction and use of transdermal patches for the delivery of pharmaceutical agents is well known in the art.

In yet another embodiment, the composition is prepared for topical administration, e.g. as an oil, ointment, gel or cream. Adjuvants for topical administration may include, for example, sodium carboxymethylcellulose, polyacrylates, polyoxyethylene-polyoxypropylene-block polymers, polyethylene glycol and wood wax alcohols. The term "gel" as used herein, refers to a substantially dilute cross-linked system, which exhibits little or no flow when in the steady-state having a solid jelly-like matrix. As contemplated herein, gel may comprise hydrogel, organogel, thermosensitive gel, non-thermosensitive gel, and aerogel. Each possibility represents a separate embodiment.

Compositions for inhalation or aspiration include solutions and suspensions in pharmaceutically acceptable aqueous or organic solvents, or mixtures thereof, as well as powders. The liquid or solid compositions may contain suitable pharmaceutically acceptable carriers or excipients as described above. The compositions may be administered by the oral or nasal respiratory route. Compositions may also be nebulized by use of inert gases. Nebulized solutions may be breathed directly from the nebulizing device or the nebulizing device may be attached to a face mask tent, or intermittent positive pressure breathing machine. Solution, suspension, or powder compositions may be administered, preferably orally or nasally, from devices (e.g. inhalers) that deliver the formulation in an appropriate manner. Currently preferred is a composition formulated for administration locally into the tissue afflicted with fibrosis. According to particular embodiments, the tissue is a lung tissue, and the administration route is intratracheal, intrabronchial, or intra-alveolar thereby affording the direct administration of the composition into the lung tissue. Each possibility represents a separate embodiment. Intratracheal administration may be facilitated by nasal prongs, a face mask, an enclosed tent or chamber (completely or semi-sealed), an intratracheal catheter, an endotracheal tube, or a tracheostomy tube as is known in the art. Each possibility represents a separate embodiment.

The pharmaceutical compositions of the present invention may exhibit release mode which may be immediate release, controlled release or a mixture thereof. Each possibility represents a separate embodiment of the invention. "Immediate release" (IR) compositions in the context of the present invention refers to compositions in which the active ingredient is released without delay following administration. "Controlled release" (CR) compositions in the context of the present invention refers to compositions in which the active ingredient is released gradually over a period of time following administration.

Therapeutic Use

According to certain aspects and embodiments, there is provided a pharmaceutical composition comprising a therapeutically effective amount of a compound of Formulae X or 1-18 including salts, hydrates, solvates, polymorphs, optical isomers, geometrical isomers, enantiomers, diastereomers, and mixtures thereof; and further comprising a pharmaceutically acceptable carrier or excipient for use as a medicament. In particular embodiments, there is provided a pharmaceutical composition comprising a therapeutically effective amount a compound of Formulae 6, 7, 8, 9, 10, 11, and 12 including salts, hydrates, solvates, polymorphs, optical isomers, geometrical isomers, enantiomers, diastereomers, and mixtures thereof; and further comprising a pharmaceutically acceptable carrier or excipient for use as a medicament. Each possibility represents a separate embodiment.

In some aspects and embodiments, the compounds and pharmaceutical compositions comprising same are useful for treating fibrosis and conditions associated therewith. In some embodiments, the compounds and compositions are useful for inhibiting (alleviating) or preventing a symptom of fibrosis. In a particular embodiment, the fibrosis is pulmonary fibrosis and the symptom is selected from the group consisting of dyspnea, cough, reduced chest expansion, bibasilar end-inspiratory dry crackles, and digital clubbing. In other embodiments, the compounds and compositions are useful for inducing apoptosis and/or reducing the survival rate of fibroblast, myofibroblast cells or epithelial cells under epithelial-mesenchymal transition (EMT) in a tissue undergoing fibrosis, thereby treating a medical condition associated with fibrosis. In yet other embodiments, the methods of the present invention comprise regaining epithelial cells under EMT, fibroblast or myofibroblast cells susceptibility to immune system surveillance, thereby treating a medical condition associated with fibrosis. In a particular embodiment, said cells are lung fibroblasts, lung myofibroblasts or lung epithelial cells under EMT. Each possibility represents a separate embodiment of the invention. In further embodiments, the compounds and compositions are useful for inhibiting SIRT1-mediated signaling in a cell selected from the group consisting of fibroblast, myofibroblast, fibrocyte and epithelial cell under EMT. Each possibility represents a separate embodiment. In yet another embodiment, said compounds are useful for inducing apoptosis and/or reducing the survival rate and/or inhibiting SIRT1-mediated signaling of other pro-fibrotic cell populations characterized by FLIP overexpression, e.g. in reprogramming epithelial cells. Each possibility represents a separate embodiment of the invention. In further embodiments, the compounds and compositions are useful in inhibiting SIRT1-mediated fibrotic activity.

As used herein, the term SIRT1-mediated signaling indicates a pathway regulated by SIRT1, including, but not limited to, anti-apoptotic signaling pathways. Without wishing to be bound by a specific theory or mechanism of action, SIRT1 can catalyze the deacetylation of acetyl lysine of histone substrate and some non-histone substrates to regulate gene expression, thereby modulating these pathways. Exemplary genes regulated by SIRT1 in IPF-lung myofibroblasts are presented in the Examples section below.

The term "fibroblast" or "fibroblasts" refers to cells derived from mesenchymal progenitor cells (or blood-borne fibrocytes) and which are present in flattened, irregular-shaped connective tissue and provide the structural framework of cell(s), ubiquitous in fibrous connective tissue by generating and/or secreting components of the extracellular matrix factors, including collagen and hyaluronic acid. The term "myofibroblast" refers to fibroblasts that transitioned from fibroblast into fibroblasts that are differentiated towards a smooth muscle cell-like phenotype, and which express high levels of alpha smooth muscle actin (αSMA) and are positive for αSMA.

Epithelial-mesenchymal transition (EMT) is a biological process in which epithelial cells lose contact adhesion and apical-basal polarity, alter their shape with dramatic cytoskeletal changes and acquire some mesenchymal features of invasion, migration and production of ECM. The presence of EMT is defined by the detection of several biomarkers that mirror the loss of epithelial phenotype and the gain of mesenchymal one, namely proteins involved in cell contact (loss of E-cadherin and gain of N-cadherin), cytoskeletal proteins (loss of cytokeratins and gain of vimentin, α-smooth muscle actin, desmin, and fibronectin) and luminal proteins secreted by the original cells (e.g., loss of surfactant production and gain of extracellular matrix or metalloproteinases secretion).

In some embodiments, the fibrosis may be pulmonary fibrosis (e.g. idiopathic pulmonary fibrosis, diffuse interstitial pulmonary fibrosis, pleural fibrosis and fibrosis associated with asthma, fibrous dysplasia, cystic fibrosis), heart fibrosis (e.g. endomyocardial fibrosis and fibrosis associated with cardiovascular disease), kidney fibrosis (e.g. associated with renal failure), dermal fibrosis (e.g. keloid), ocular fibrosis, mucosal fibrosis, fibrosis of the central nervous system, fibrosis in bone or bone marrow, fibrosis in an endocrine organ (e.g. pancreas) or fibrosis in the gastro-intestinal system. Each possibility represents a separate embodiment of the invention.

In various specific embodiments, the fibrosis is associated with a disorder selected from the group consisting of: cystic fibrosis, endomyocardial fibrosis, idiopathic pulmonary fibrosis, mediastinal fibrosis, pleural fibrosis, postfibrinous fibrosis, proliferative fibrosis, and retroperitoneal fibrosis, wherein each possibility represents a separate embodiment of the invention. In a particular embodiment, the fibrosis is associated with a disorder selected from the group consisting of: cystic fibrosis, endomyocardial fibrosis, mediastinal fibrosis, pleural fibrosis, postfibrinous fibrosis, proliferative fibrosis, and retroperitoneal fibrosis. In another embodiment, the fibrosis is associated with diffuse interstitial pulmonary fibrosis. In yet another embodiment, the fibrosis is pancreatic fibrosis. In another embodiment, the fibrosis is dermal fibrosis (e.g. scarring or abnormal wound healing). In another embodiment, the fibrosis is associated with an autoimmune disease, e.g. systemic lupus erythematosus (SLE), Sjogren syndrome, or diffuse systemic sclerosis with scleroderma.

In other embodiments, the compounds and compositions of the invention are useful in treating or inhibiting fibrosis associated with exposure to poisons or toxins, exposure to drugs (e.g. chemotherapy), irradiation, burns, fibrosis and scarring or abnormal wound healing following surgery or injury, immune reactions, infection, foreign bodies (e.g. mechanical implants), and genetically determined sensitivities to a certain substance. Thus, in some embodiments, the compositions and methods of the invention are useful for treating an interstitial lung disease (ILD) associated with exposure to an agent or etiology as disclosed herein.

Examples of fibrosis also include, but are not limited to, vascular fibrosis, pulmonary fibrosis (e.g., idiopathic pulmonary fibrosis), pancreatic fibrosis, liver fibrosis (e.g., cirrhosis or following hepatitis C virus infection), renal fibrosis (e.g., interstitial fibrosis in focal segmental glomerulosclerosis and nephrogenic systemic fibrosis), musculoskeletal fibrosis, cardiac fibrosis (e.g., endomyocardial fibrosis, idiopathic myocardiopathy), skin fibrosis (e.g., scleroderma, post-traumatic, operative cutaneous scarring, keloids and cutaneous keloid formation), eye fibrosis (e.g., glaucoma, sclerosis of the eyes, conjunctival and corneal scarring, and pterygium), progressive systemic sclerosis (PSS), Peyronie's disease, idiopathic and pharmacologically induced retroperitoneal fibrosis, mediastinal fibrosis, fibrosis associated with a surgery, intestinal fibrosis (e.g., Crohn's disease which can cause fibrosis of the intestinal wall), fibrosis associated with a surgical implantation of an artificial organ, spleen fibrosis (e.g., sickle-cell anemia may cause enlargement and ultimately fibrosis of the spleen), fibrosis associated with rheumatoid arthritis, fibrosis associated with Wilson's disease, fibrosis associated with alcoholism, fibrosis associated with exposure to toxins or to chemotherapeutic agents, fibrosis associated with metabolic disorders, fibrosis associated with irradiation, and fibrosis associated with inflammation. Each possibility represents a separate embodiment. According to one embodiment, fibrosis is pulmonary fibrosis. According to another embodiment, pulmonary fibrosis comprises idiopathic pulmonary fibrosis.

Fibrosis may be diagnosed in a subject using methods known to one of ordinary skill in the art. For example, fibrosis may be diagnosed using routine blood chemistry analysis, ultrasound, radiography, CT, MRI, biopsy and histological examination, capable of evaluating the fibrotic pathology. For example, without limitation, fibrotic pathology may be manifested by abnormal accumulation of fibroblasts within a tissue or organ, abnormal or excessive production of connective tissue (e.g. deposition of collagen and/or other extracellular matrix (ECM) proteins), and subsequent structural alterations including thickening, stiffening, and scarring of said tissue or organ. Genetic testing (e.g., of the CFTR gene), as well as clinical evaluation of symptoms and manifestations of fibrosis (e.g. lung function parameters) may also be used in the diagnosis and prognosis of fibrosis and fibrotic conditions.

In additional embodiments, the compounds and compositions are useful in treating a fibrotic disorder. Fibrotic disorders within the scope of the present invention may be associated with pulmonary fibrosis (e.g. idiopathic pulmonary fibrosis, diffuse interstitial pulmonary fibrosis, pleural fibrosis and fibrosis associated with asthma, fibrous dysplasia, cystic fibrosis), heart fibrosis (e.g. endomyocardial fibrosis and fibrosis associated with cardiovascular disease), kidney fibrosis (e.g. associated with renal failure), dermal fibrosis (e.g. keloid), ocular fibrosis, mucosal fibrosis, fibrosis of the central nervous system, fibrosis in bone or bone marrow, fibrosis in an endocrine organ (e.g. pancreas) and/or fibrosis in the gastro-intestinal system. Each possibility represents a separate embodiment of the invention. In various specific embodiments, the fibrotic disorder is selected from the group consisting of: cystic fibrosis, endomyocardial fibrosis, idiopathic pulmonary fibrosis, mediastinal fibrosis, pleural fibrosis, postfibrinous fibrosis, proliferative fibrosis, and retroperitoneal fibrosis, wherein each possibility represents a separate embodiment of the invention. In a particular embodiment, the fibrotic disorder is selected from the group consisting of: cystic fibrosis, endomyocardial fibrosis, mediastinal fibrosis, pleural fibrosis, postfibrinous fibrosis, proliferative fibrosis, and retroperitoneal fibrosis. In another embodiment, the fibrotic disorder is diffuse interstitial pulmonary fibrosis. In yet another embodiment, the fibrotic disorder is associated with pancreatic fibrosis. In another embodiment, the fibrotic disorder is associated with dermal fibrosis (e.g. scarring or abnormal wound healing). In another embodiment, the fibrotic disorder is an autoimmune disease, e.g. systemic lupus erythematosus (SLE), Sjogren syndrome, or diffuse systemic sclerosis with scleroderma.

In some embodiments, the conditions to be treated in accordance with the invention are SIRT1-mediated. In other embodiments, the conditions are HDAC8-mediated. In yet other embodiments, the conditions have not been diagnosed as being mediated by cyclooxygenase and/or lipoxygenase enzymes of the mammalian arachidonic acid metabolism. As used herein, an enzyme (e.g. SIRT1 or HDAC8)-mediated disease or condition refers to a disease or condition in which the enzymatic activity contributes to the etiology or pathology. Such conditions include those in which the enzymatic (e.g. acetylase) activity is necessary and/or sufficient for the manifestation of the symptoms of the disease, state or condition (or its etiology or progression), and in particular to those caused by or exacerbated by, dysregulated or aberrant expression (e.g. overexpression) or activity of SIRT1 or HDAC8. Similarly, an enzyme (e.g. SIRT1)-mediated fibrotic activity indicates that the activity leading to enhanced or accelerated fibrosis is caused by or exacerbated by the enzyme. In some embodiments, said condition is other than an obstructive lung disease (e.g. asthma), an allergic condition, a tumor, an autoimmune disorder, blood platelet aggregation or coronary infarction. Each possibility represents a separate embodiment of the invention.

It is to be understood, that a subject to be treated is typically afflicted with fibrosis, or in some embodiments has been determined by the treating physician to be at high risk for developing fibrosis, requiring anti-fibrotic therapy. For example, severe, treatment-resistant asthma, may eventually lead to the development of fibrosis, which may be treated in accordance with embodiments of the invention. It is to be understood, that other forms of asthma that are not commonly associated with fibrosis, such as mild forms of allergic asthma and bronchial asthma, may be addressed by conventional therapies and do not generally require anti-fibrotic therapy.

As used herein, the terms "treating fibrosis" and "treating a fibrotic disorder" include, but are not limited to, alleviation of symptoms associated with fibrosis-related pathology or condition and/or prolonging the health or survival of the subject being treated beyond that expected in the absence of such treatment. The term "treating fibrosis" further refers to reduction in the level or extent of fibrotic pathology, measurable using various clinical and diagnostic methods known in the art, e.g. as disclosed and exemplified herein.

In some embodiments the treatment includes partial or complete resolution of the fibrotic state. Accordingly, in some embodiments, the compounds of the invention are capable of enhancing, promoting or inducing fibrosis-resolution. In other embodiments, the invention relates to methods of enhancing, promoting or inducing resolution in a subject afflicted with fibrosis, comprising administering to the subject a pharmaceutical composition comprising a therapeutically effective amount of a compound of Formula X or any one of Formulae 1-18 as disclosed herein. In another embodiment, said fibrosis is non-resolving fibrosis (e.g. severe fibrosis, or fibrosis that is resistant to existing anti-fibrotic therapies). In another embodiment, said fibrosis is pulmonary fibrosis. In yet another embodiment, said fibrosis is associated with a condition as disclosed herein. In a particular embodiment, said subject is afflicted with IPF or another ILD.

Although fibrosis was previously thought to be irreversible, recent evidence indicates that certain circumstances permit the resolution of fibrosis when the underlying causes of injury are eradicated. For example, resolution of fibrosis may involve degradation and removal of the fibrotic ECM, and elimination or attenuation of fibrogenic myofibroblasts. However, effective and safe therapies for promoting fibrosis resolution are lacking. The invention in certain embodiments thereof refers to compounds and methods capable of not only attenuating the development or exacerbation of fibrosis, but also of facilitating fibrosis resolution, characterized by reduction of existing fibrotic tissue, ECM deposits and/or fibrogenic myofibroblasts.

As used herein, the term "administering" refers to bringing in contact with the compound and/or composition of the present invention. Administration can be accomplished to living organisms, for example humans.

A "therapeutic" treatment is a treatment administered to a subject who exhibits signs of pathology for the purpose of diminishing or eliminating those signs. A "therapeutically effective amount" is that amount of compound which is sufficient to provide a beneficial effect to the subject to which the compound is administered. The precise dose to be employed in the pharmaceutical composition comprising a compound of any of Formulae X or 1-18 will depend on the route of administration, and the seriousness of the disease, and should be decided according to the judgment of the practitioner and each patient's circumstances. A preferred dosage will be within the range of about 0.01-1000 mg/kg of body weight, about 0.1 mg/kg to 100 mg/kg, about 1 mg/kg to 100 mg/kg, about 10 mg/kg to 75 mg/kg, about 0.1 to 1 mg/kg etc., including each value within the specified ranges. Exemplary non-limiting amounts of the compound of any of Formulae X or 1-18 include about 0.1 mg/kg, about 0.2 mg/kg, about 0.5 mg/kg, about 1 mg/kg, about 5 mg/kg, about 10 mg/kg, about 20 mg/kg, about 50 mg/kg, about 60 mg/kg, about 75 mg/kg, and about 100 mg/kg. Each possibility represents a separate embodiment. Alternatively, the amount administered can be measured and expressed as molarity of the administered compound. By way of illustration and not limitation, the compound of any of Formulae X or 1-18 can be administered in a range of about 0.1 to 10 mM, including each value within the specified range e.g., about 0.1, 0.25, 0.5, 1 or 2 mM. Each possibility represents a separate embodiment. Alternatively, the amount administered can be measured and expressed as mg/ml, μg/ml, or ng/ml.

The administration schedule will depend on several factors such as the severity and progression of the disorder, age, weight etc. For example, the compositions of the invention can be taken once-daily, twice-daily, thrice daily, once-weekly or once-monthly. In addition, the administration can be continuous, i.e., every day, or intermittent. The terms "intermittent" or "intermittently" as used herein means stopping and starting at either regular or irregular intervals. For example, intermittent administration can be administration one to six days per week or it may mean administration in cycles (e.g. daily administration for two to eight consecutive weeks, then a rest period with no administration for up to one week) or it may mean administration on alternate days. The effectiveness of said compositions could enable a shortened period of treatment with superior results.

Although the pharmaceutical composition comprising a compound of any of Formulae X or 1-18 may be administered as the single therapeutic agent, combination therapy including co-administration with one or more additional HDAC inhibitors is within the scope of the present invention. Co-administration of a compound of any of Formulae X or 1-18 with one or more therapeutic agents may take place sequentially in any order, simultaneously or a combination thereof. For example, administration of a compound of any of Formulae X or 1-18 can take place prior to, after or at the same time as the administration of the additional therapeutic agent(s). For example, a total treatment period can be decided for the compound of any of Formulae X or 1-18. The additional agent(s) can be administered prior to the onset of treatment with the compound of any of Formulae X or 1-18 or following treatment with the compound of any of Formulae X or 1-18. In addition, the additional agent(s) can be administered during the period of administering the compound of any of Formulae X or 1-18 but does not need to occur over the entire treatment period. In another embodiment, the treatment regimen includes pre-treatment with one agent, followed by the addition of the other agent or agents. Alternating sequences of administration are also contemplated. Alternating administration includes administration of a compound of any of Formulae X or 1-18, followed by the additional agent, followed by a compound of any of Formulae X or 1-18, etc. The aforementioned sequences can also be administrated in several cycles wherein each cycle may be similar or different with each possibility representing a separate embodiment. The therapeutic efficacy of the combination of the compound of any of Formulae X or 1-18 and the additional agent(s) is at least additive. In some embodiments, the therapeutic efficacy is synergistic, namely the overall dose of each of the components may be lower, thus resulting in significantly lower side effects experienced by the subject, while a sufficient desirable therapeutic effect is nonetheless achieved. When combination therapy is involved, the compound of any of Formulae X or 1-18 and the additional therapeutic agent(s) may be provided in a single dosage form such as a fixed-dose combination or in separate compositions intended for simultaneous administration.

The one or more additional HDAC inhibitors include, but are not limited to, Trichostatin A, Suberanilohydroxamic Acid (SAHA; Vorinostat), CRA-026440, CRA-024781, M344, Rocilinostat (ACY-1215), Pyroxamide, Suberohydroxamic acid (SBHA), Tubacin, Scriptaid, CBHA, Panobinostat, Pracinostat, Belinostat, and a mixture or combination thereof. Each possibility represents a separate embodiment.

In some embodiments, there is provided a method of treating or inhibiting fibrosis in a subject in need thereof, the method comprising administering to the subject a pharmaceutical composition comprising a therapeutically effective amount of a compound of Formula X as defined herein. In one embodiment, said compound downregulates SIRT1-mediated deacetylase activity (to a statistically significant extent measurable e.g. by enhanced levels of acetylated SIRT1 substrates as disclosed herein). Methods of evaluating downregulation of SIRT1-mediated deacetylase activity are known in the art, and include, for example, various immunoassays e.g. Western blot, immunoprecipitation, or luminescent assays using luminogenic peptide substrates that can be deacetylated by SIRT activities, such as those available by Promega. In another embodiment, said compound inhibits (to a statistically significant extent) SIRT1-mediated lysine residue deacetylation on Ku70. In another embodiment said compound is capable of specifically binding a binding pocket on SIRT1 protein comprising at least one of $Val^{412}$ (main chain) and $His^{363}$ (side chain). The term specifically binding as used herein indicates that the compound binds to the target (e.g. binding pocket) under physiological conditions, without being subjected to competitive inhibition by an unrelated substance.

Pulmonary Fibrosis and Special Patient Populations

Among the patient populations for which the compositions and methods of the invention are particularly beneficial, are those afflicted with pulmonary fibrosis, in particular subjects diagnosed with idiopathic pulmonary fibrosis (IPF) and other interstitial lung diseases (ILD). In some embodiments, the teachings of the invention provide for the treatment of new patient populations, not previously considered amenable for anti-fibrotic treatment, as described herein.

In another embodiment, there is provided a method for treating a condition associated with pulmonary fibrosis in a subject in need thereof, the method comprising administering to the subject a composition comprising a therapeutically effective amount of a compound represented by the structure of Formula X as defined herein. In one embodiment the treatment inhibits (or reverses) a symptom of fibrosis in said subject. In another embodiment said subject is afflicted (or diagnosed) with pulmonary fibrosis. In another embodiment said subject is afflicted with pulmonary fibrosis and said compound is administered by intratracheal, intrabronchial, or intra-alveolar administration.

ILD is a heterogeneous group of disorders characterized by alveolar septal thickening, fibroblast proliferation, collagen deposition, and, if the process remains unchecked, pulmonary fibrosis. Among the possible causes of ILD are connective tissue disorders (e.g. ILD secondary to systemic diseases), occupational or environmental lung exposures (e.g. silicosis) and certain drugs (e.g. bleomycin). ILD of unknown causes (idiopathic ILD) can be diagnosed either by characteristic clinical features or presentation (e.g. sarcoidosis) or by histology following lung tissue biopsy. The disorders distinguished primarily by characteristic histopathologic features are termed the idiopathic interstitial pneumonias (IIP).

IPF, identified histologically as usual interstitial pneumonia, is the most common form of IIP. Other IIP include nonspecific interstitial pneumonia (NSIP), which is histologically similar to IPF, and six other subtypes characterized by varying degrees of interstitial inflammation and fibrosis. All IIP cause dyspnea and diffuse abnormalities on high-resolution CT. Cough and dyspnea on exertion are typical symptoms in these patients, including IPF patients and other subjects with pulmonary fibrosis, with variable onset and progression. Common other signs include tachypnea, reduced chest expansion, bibasilar end-inspiratory dry crackles, and digital clubbing. The classic sign of IPF is fine, dry, inspiratory crackles (Velcro crackles) at both bases.

Diagnosis of IPF is based on history, physical examination, high-resolution CT, and/or lung biopsy, if necessary. Most patients have moderate to advanced clinical disease at the time of diagnosis and deteriorate despite treatment. Several prognostic models for IPF have been proposed. Among the factors that portend a worse prognosis are older age, male sex, and reduced lung functions manifested by lower forced vital capacity and lower diffusing capacity, as explained in further detail below.

ILD are defined as restrictive lung diseases, namely diseases that restrict lung expansion, resulting in a decreased lung volume, an increased work of breathing, and inadequate ventilation and/or oxygenation. Pulmonary function test demonstrates a decrease in the forced vital capacity, (FVC), namely in the volume of air that can forcibly be blown out after full inspiration. In contradistinction, obstructive lung diseases (e.g. asthma, COPD, chronic bronchitis and cystic fibrosis) characterized by airway obstruction, in which the vital capacity often remains relatively normal. Thus, FVC is commonly used in differential diagnosis of lung diseases, such as between restrictive and obstructive lung diseases.

Another type of pulmonary function tests is diffusing capacity (conveniently measured as transfer factor of the lung for carbon monoxide, DLCO), measuring the carbon monoxide uptake from a single inspiration in a standard time (usually 10 seconds), reflecting the extent to which oxygen passes from the air sacs of the lungs into the blood. In general, a healthy individual has a value of DLCO between 75% and 125% of the average. Lung fibrosis is generally characterized by diffusion impairments, characterized by DLCO values of between.

In general, anti-fibrotic treatments are currently indicated in patients presented with partly impaired lung functions, as evaluated by DLCO and FVC parameters. As current anti-fibrotic treatments aim at preventing or delaying the deterioration and cannot reverse or treat existing fibrotic damage or pathology, only subjects characterized by DLCO of at least 30% of the average are currently considered amenable for treatment. Typically, currently available anti-fibrotic treatments are provided to patients characterized by DLCO of between 30% and 80%. Further, FVC values of at least 50% are generally considered fundamental for a successful anti-inflammatory treatment, and currently available anti-fibrotic treatments are provided to patients characterized by FVC of at least 50%.

It is herein unexpectedly disclosed, that compositions and methods are capable of reversing or resolving an existing fibrotic state or pathology, and are also suitable for treatment of patients with severely impaired pulmonary functions, that were not hitherto amenable for treatment. Thus, in some embodiments of the invention, the treatment of patients with pulmonary fibrosis and impaired lung functions, characterized by DLCO<30% and/or FVC<50%, is contemplated. In another embodiment, compositions and methods of the invention are used for enhancing the DLCO and/or FVC values of the treated subject. Each possibility represents a separate embodiment of the invention.

The following examples describe specific aspects of the invention to illustrate the invention and provide a description of the present methods for those skilled in the art. As used herein and in the appended claims, the singular forms "a", "an", and "the" include plural references unless the context clearly dictates otherwise. Thus, for example, reference to "a compound represented by the structure of Formula X" includes a plurality of such compounds. It should be noted that the term "and" or the term "or" is generally employed in its sense including "and/or" unless the context clearly dictates otherwise. As used herein, the term "about" is meant to encompass variations of ±10%.

EXAMPLES

Materials and Methods

Human lung myofibroblasts Differentiated fibroblasts from IPF-lungs and controls from patient lung biopsies performed for tumor diagnosis were obtained under a protocol detailed in Wallach-Dayan et al., J. Autoimmun. 59: 67-76, 2015. LL 97A (AlMy) (ATCC® CCL-191™)-IPF-lung, and LL 24 (ATCC® CCL-151™)-normal lung fibroblast cell lines were used.

Animals C57BL/6 and mutant mice, male, 11-12 weeks old (Harlan Sprague Dawley, Indianapolis, IN, USA) were used. SIRT1 dominant-negative mice carry a point mutation (H355Y), $Sirt1^{tm2.1Mcby}$ ($Sirt1^{y/y}$, RBRC05324, RIKEN Bio Resource Center, Japan) that ablates SIRT1 enzymatic activity, described in Gabay et al., Arthritis Rheum. 65: 159-166, 2013; and Seifert et al., FASEB J. 26: 555-566, 2012. Mice were maintained under specific pathogen-free conditions with adherence to institutional guidelines for the care and use of laboratory animals. Chimeric mice with SIRT1-deficient mice and WT hematopoietic cells were generated as described in Golan-Gerstl et al., Am. J. Respir Cell Mol. Biol. 36: 270-275, 2007.

Oropharyngeal aspiration (OA) and induction of lung fibrosis in mice Oropharyngeal aspiration of BLM (OA-BLM) was performed as detailed in Golan-Gerstl et al., Am. J. Respir. Cell Mol. Biol. 36: 270-275, 2007. Lung fibrosis was assessed via semi-quantitative morphological index (Wallach-Dayan et al., PNAS USA 104: 20460-20465, 2007). Lung collagen was measured using a Sircol Collagen Assay kit (Biocolor, Belfast, Northern Ireland), and standard protocol of trichrome staining. Isolation of mouse lung myofibroblasts Myofibroblast isolation and culture was performed as described in Golan-Gerstl et al., Am. J. Respir. Cell Mol. Biol. 36: 270-275, 2007; and Wallach-Dayan et al., PNAS USA 104: 20460-20465, 2007.

Cell death and apoptosis Apoptosis was assessed with Annexin V affinity labeling, trypan blue exclusion, and caspase-3 cleavage in WB as described in Golan-Gerstl et al., Am. J. Respir. Cell Mol. Biol. 36: 270-275, 2007; Wallach-Dayan et al., PNAS USA 104: 20460-20465, 2007; and Wallach-Dayan et al., Am. J. Physiol. Lung Cell Mol. Physiol. 290: L790-L796, 2006.

Immunohistochemistry (IHC) staining of lung tissue sections was performed as described in Golan-Gerstl et al., Am. J. Respir Cell Mol. Biol. 36: 270-275, 2007; and Wallach-Dayan et al., PNAS USA 104: 20460-20465, 2007.

FLIP protein in lung myofibroblasts Standard WB and flow cytometry were performed as described in Cohen et al., Am. J. Respir. Cell Mol. Biol. 40: 231-238, 2009.

Immunoprecipitation and immunoblotting Standard protocols were performed as described in Golan-Gerstl et al., Am. J. Respir. Cell Mol. Biol. 47: 271-279, 2012.

FLIP up/downregulation FLIP-long cDNA expression vector and control (pcDNA3.1 vector alone) were used. Using the Digital Bio Technology transfection kit (Cat #MPK-1096) and microporator (Seoul, Korea), a mixture of 12 μl of "Solution R" (transfection kit), and 2 μg of plasmid containing the $FLIP_L$ cDNA, were added to $5\times10^5$ $FLIP^{low}$ fibroblasts. shRNA was designed to target the common coding region of short- and long FLIP variants according to the FLIP mRNA sequence from the GeneBank (NM009805). The sequence was designed to form 5' overhangs on each side for direct ligation into the vector (Integrated DNA Technologies, Coralville, IA, USA).

```
Top strand (SEQ ID NO: 1):
CGCGTCCCCGAATAGACTTGAACACAAATTCAAG

AGATTTGTGTTCAAGTCTATTCTTTTTGGAAAT.

Bottom strand (SEQ ID NO: 2):
AGGGGCTTATCTGAACTTGTGTTTAAGTTCTCTA

AACACAAGTTCAGATAAGAAAAACCTTTAGC.
```

The GFP+pLVTHM lentiviral vector was used. Mouse lungs had undergone direct lung transduction by OA and $FLIP^{high}$. Myofibroblasts were transduced for 24 h with lentivirus with a multiplicity of infection (MOI) of 200 in the presence of 8 μg of polybrene (Sigma Aldrich), washed, and cultured in 10% RPMI (Sigma Aldrich). Cells were harvested after 1 week.

Docking CMH into SIRT1 AutoDock VINA v.1.1.2 was used (Trott et al., J. Comp. Chem. 31: 455-461, 2010) based on human SIRT1 crystal structure from the Protein Data Bank (PDB entry 4zzj). Both ligands and water molecules in 4zzj were removed using the Discovery Studio Visualizer 4.5. Hydrogen atoms were added using the MolProbity server (Chen et al., Acta Crystallo. D, Biol. Cryst. 66: 12-21, 2010). Kollman united atom-type charges, and solvation parameters were added to the model with the aid of AutoDockTools 1.5.6 (Morris et al., J. Comp. Chem. 30: 2785-2791, 2009). CMH structure was obtained from PubChem database. Partial charges of the ligands were assigned using Gasteiger-Marsili method with the aid of AutoDockTools. The AutoDock Vina parameter "Exhaustiveness", which determines how comprehensively the program searches for the lowest energy conformation, was set to a high value, 18, and the size of grid box was set as 22 Å×16 Å×20 Å for covering the catalytic site. Ligand rotatable torsions were released.

mRNA sequencing (RNA-seq) data analysis RNA-seq data was created by Ion Torrent sequencing and a gene expression machine (Vukmirovic et al., BMC Pul. Med. 17: 15, 2017) and analyzed by Tuxedo Suite, TopHat and Cufflinks, as detailed in Ghosh et al., Meth. Mol. Biol. 1374: 339-36, 2016; Kim et al., Gen. Biol. 14: R36, 2013; and Song et al., GMR 14: 18268-182796, 2015. In particular, BAM files and Tophat2 software were used to map differences in gene expression to the hg19 reference genome, and then Cufflink was used to create the fpkm dataset and heat maps. MetaCore data pathway enrichment analysis generated pathway maps for SIRT1 apoptosis/survival and Fas-death receptor cascades and p53 signaling as detailed in Woltmann et al., PLoS One 9: e98229, 2014. Up- or down-regulated gene expression in IPF-fibroblasts following CMH treatment was analyzed, and fold change ≥2 was recorded and identified.

Data analysis and statistics The Kruskall-Wallis test was applied to compare variables measured at different time intervals or following different treatments. The Mann-Whitney test with the Bonferroni correction was used to test for statistical significance. Two-way ANOVA was used to assess time and treatment effects and interactions.

Figure 1B:
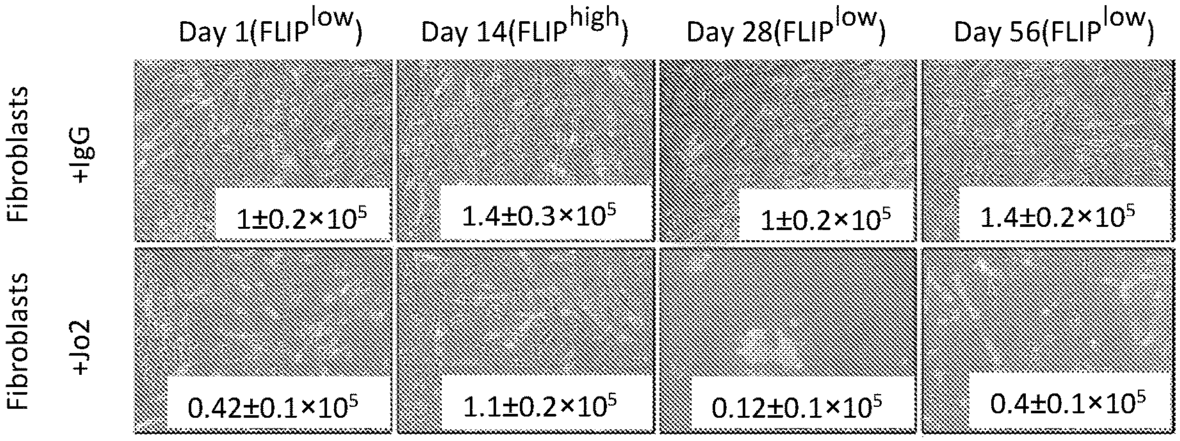
Figure 1C:
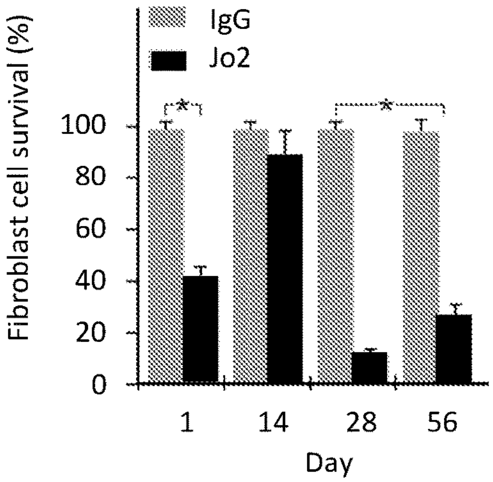

Example 1: Lungs of BLM-Treated Mice Resolving Fibrosis Decrease FLIP and Myofibroblasts Regain Susceptibility to Apoptosis FLIP kinetics, at resolution of BLM injury, was evaluated as detailed in Wallach-Dayan et al., J. Autoimmun. 59: 67-7, 2015. FLIP was shown to return to baseline during lung resolution (FIG. 1A; days 28, 56). Myofibroblasts underwent apoptosis, as did baseline pre-fibrosis lung myofibroblasts (day 1). Their number decreased from a peak of 1-1.4×$10^5$ (fibroblasts+IgG) to only 0.12-0.42×$10^5$ (fibroblasts +Jo2) while the number of fibrotic-lung myofibroblasts, in co-culture, remained constant (i.e. 1.4-1.1×$10^5$), (FIGS. 1B-1C).

Figure 2A:
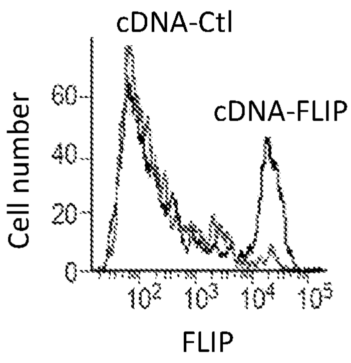
FIG. 2A-2G. Critical role of FLIP in myofibroblast resistance to apoptosis and BLM-induced lung fibrosis.
Figure 2B:
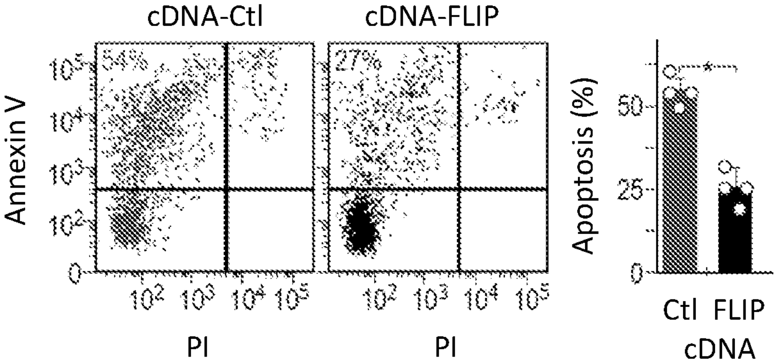
Figure 2C:
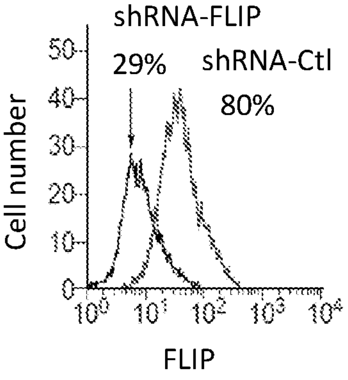
Figure 2D:
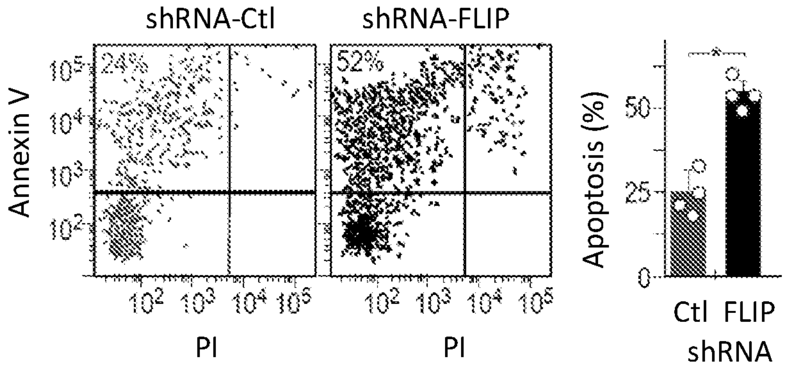
Figure 2E:
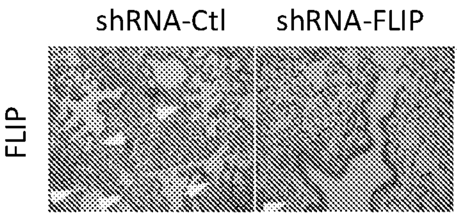
Figure 2F:
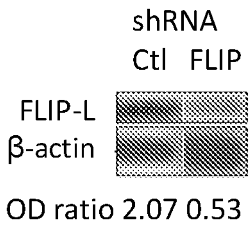

Example 2: FLIP Downregulation is Important to Regain Fibrotic-Lung Myofibroblast Predisposition to Apoptosis and for Attenuation of Lung Fibrosis FLIP was overexpressed in FLIP$^{low}$ myofibroblasts from lungs resolving fibrosis. Changes were determined by flow cytometry (FIG. 2A) as described in Wallach-Dayan et al., Mol. Cancer Ther. 7: 1615-1623, 2008. FLIP was down-regulated via FLIP shRNA GFP lentiviral vector (Wilson et al., Mol. Ther. 21: 825-833, 2013) in initially FLIP$^{high}$ myofibroblasts from fibrotic lungs (FIG. 2C). Transfectants were exposed to apoptosis-inducer Jo2 monoclonal antibody (mAb) and analyzed by Annexin V staining (FIG. 2B). FLIP overexpression (FIG. 2A, cDNA-FLIP) decreased apoptosis by 50% compared to controls (cDNA-Ctl) (FIG. 2B). In contrast, FLIP downregulation by shRNA (FIG. 2C, shRNA-FLIP) doubled the number of apoptotic cells (shRNA-Ctl), (FIG. 2D). The data suggests that FLIP has an important role in regulation of lung myofibroblast apoptosis during fibrosis.

Figure 2G:
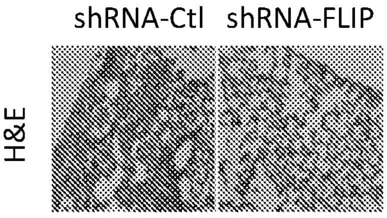

On day 6 post-oropharyngeal aspiration (OA) of BLM, FLIP shRNA GFP$^+$ or control SHAM lentiviral vector (2×$10^8$TU/ml) mixed with 5% lipofectamine (Invitrogen, Carlsbad CA, USA) was administered to C57BL/6 mice in a second OA. SHAM lentiviral vector was administered into additional control-BLM-treated mice. Primarily, the expression of FLIP shRNA GFP vector in vivo in lung tissue sections in cells with the morphology and interstitial location of fibroblasts was verified using specific anti-GFP mAb in immunohistochemistry (IHC), and in flow cytometry of fibroblasts isolated from these mice lungs, showing GFP expression and quantification as 26% of total lung cells. The shRNA, compared to control (shRNA-Ctl), downregulated FLIP in vivo in cells with the morphology and interstitial location of fibroblasts by IHC (FIG. 2E) and in isolated GFP lung myofibroblasts as assessed in vitro by Western blot (WB) (FIG. 2F), and ameliorated fibrosis detected by hematoxylin and eosin (H&E; FIG. 2G). The data indicates the important role of myofibroblast FLIP levels in lung fibrosis evolution. FLIP expression is decreased in lungs of BLM-treated mice resolving fibrosis, where myofibroblasts regain susceptibility to apoptosis (FIGS. 1A-1C and 2A-2G).

Figure 3A:
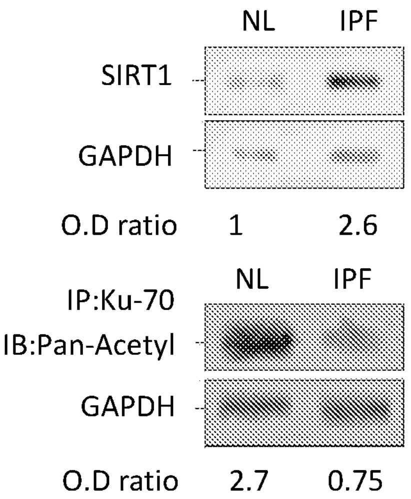
Figure 3B:
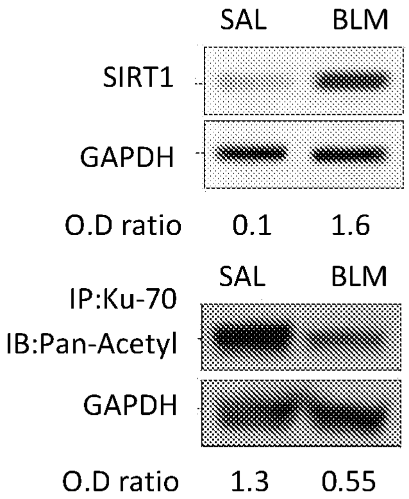
Figure 3C:
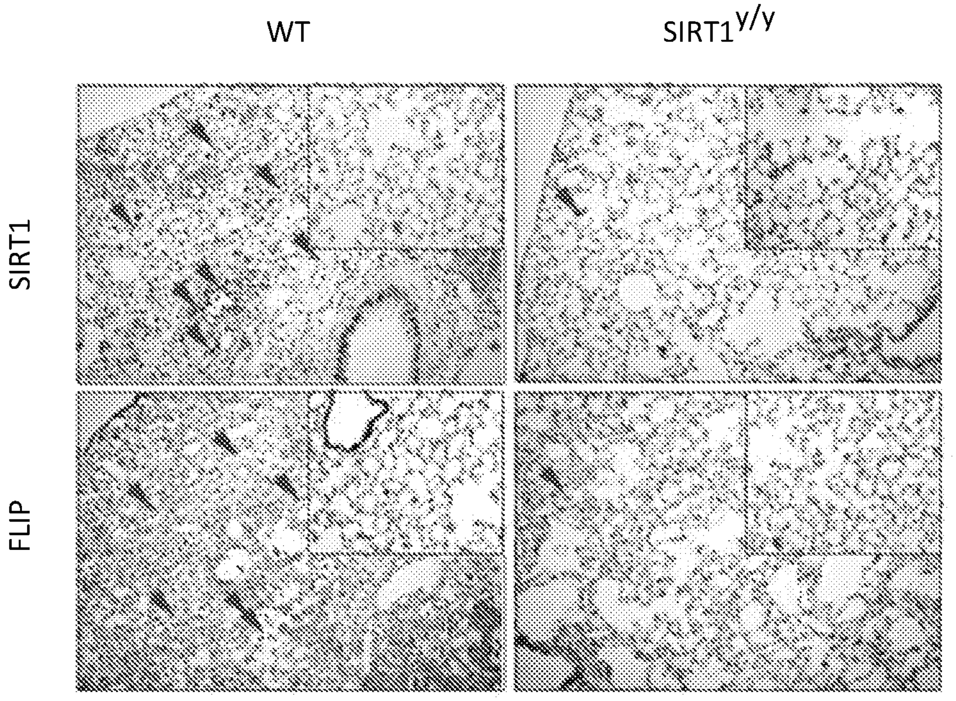

Example 3: SIRT1 and Ku70-Deacetylation are Increased in IPF- As Well as in BLM-Lung Myofibroblasts, and BLM-Treated Chimeric Mice with Deficient SIRT1, Specifically in Myofibroblasts, Downregulate FLIP and Show Less Fibrosis FLIP$^{high}$ myofibroblasts from both humans with IPF (FIG. 3A) and BLM-treated mice lungs (FIG. 3B) have increased SIRT1 (FIG. 3A-B, upper panels) with reduced Ku70 acetylation (FIGS. 3A-3B, lower panels) when compared to their normal counterparts ("IPF vs. NL" or "BLM vs. SAL"). A regulatory role of SIRT1 on FLIP in fibroblasts during lung fibrosis, using BLM-treated SIRT1$^{y/y}$ chimeric mice with normal immune cells and mesenchymal cells bearing inactive SIRT1 was determined. 14 days of BLM-treatment, SIRT1$^{y/y}$ vs. WT control chimeric mice had significantly lower FLIP levels, as assessed by IHC (FIG. 3C, lower panels); and reduced fibrosis, as determined by H&E and collagen-trichrome staining in lung tissue sections (FIG. 3D, upper and lower panels, respectively). However, saline-treated mice showed no differences in fibrosis markers or FLIP between SIRT1$^{y/y}$ and WT (FIG. 3C, inserts in lower and upper panels). Semi-quantitative morphological index (SMI) grading of H&E-stained sections showed a 30% reduction in SIRT1$^{y/y}$ in fibrosis (FIG. 3E). Soluble collagen content, in Sircol assay, was decreased in more than 50% (FIG. 3F) and lymphocytes in bronchoalveolar analysis from an average of 26% to only 4%. Thus, poor SIRT1 activity in myofibroblasts plays an important role in FLIP destabilization and drives fibrosis resolution. Without being bound by any theory or mechanism of action, FLIP accumulation in fibrotic-lung fibroblasts is associated with SIRT1-mediated Ku70-deacetylation, which further leads to fibrosis evolution.

Figure 4A:
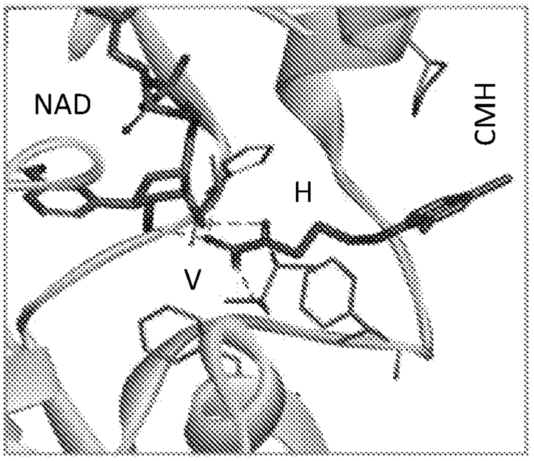
FIG. 4A-4G. CMH docking into SIRT1 and CMH effects on FLIP expression, Ku70 acetylation, and Ku70/FLIP complex, in human IPF-lung myofibroblasts. Docking assessment by AutoDock VINA v.1.1.2.
Figure 4B:
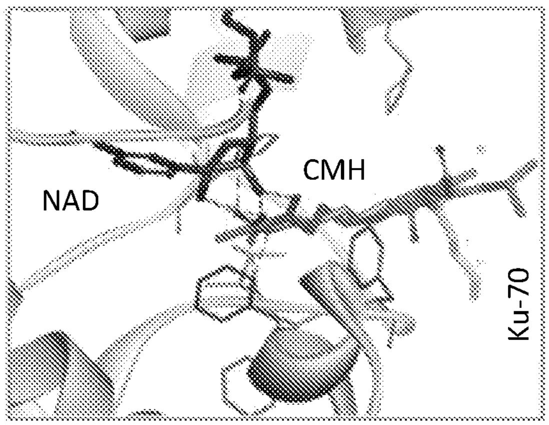
Figure 4C:
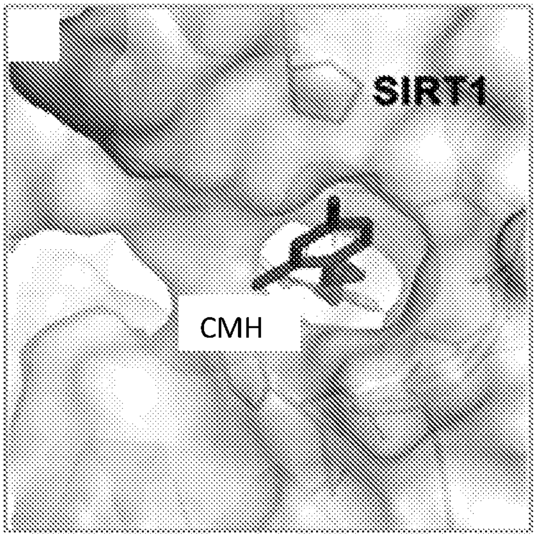

Example 4: CMH Docks into SIRT1 Lysine Binding-Site and Inhibits Ku70 Deacetylation, Destabilizes Ku70/FLIP Complex and Downregulates FLIP in IPF-Lung Myofibroblasts As determined In-silico by AutoDock VINA v.1.1.2 (Trott et al., J. Comp. Chem. 31: 455-461, 2010), 4-(4-Chloro-2-methylphenoxy)-N-hydroxybutanamide (CMH) docked into a narrow hydrophobic pocket in SIRT1 (FIG. 4A-C). Hydroxamate moiety created four hydrogen bonds: two between CMH and the NAD cofactor, one with the main-chain carbonyl of Val$^{412}$ (V), and one between the His$^{363}$ (H) side chain of SIRT1 and CMH (FIG. 4A). The predicted CMH binding mode is unexpectedly highly similar to the acetylated lysine substrate-binding mode, as determined by superimposition of CMH in the crystallographic structure and described substrate (FIG. 4B). CMH fits surprisingly well in the narrow binding pocket (FIG. 4C) suggesting CMH as a previously unrecognized SIRT1 inhibitor. While CMH docking into the lysine-substrate binding site on SIRT1 was performed in isolation and the predicted binding energy was not presented in relation to a drug of known activity or an endogenous substrate (acetylated Lys) as a reference, the docking nevertheless suggests that SIRT1 may be inhibited by CMH.

Figure 4D:
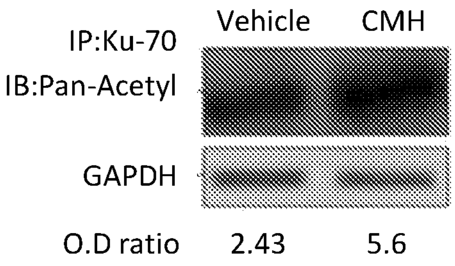
Figure 4E:
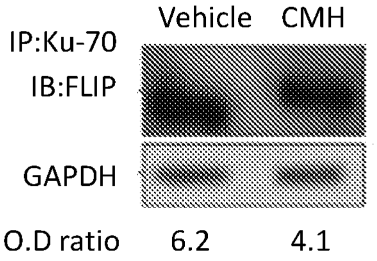
Figure 4F:
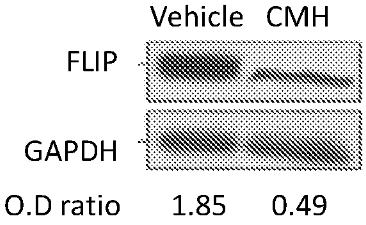
Figure 4G:
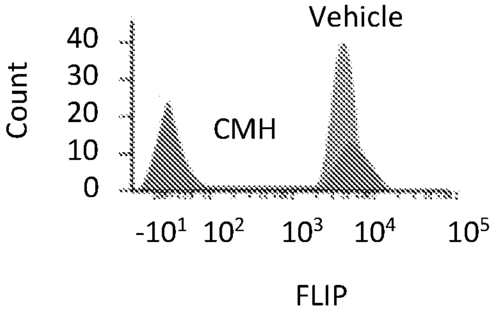

Indeed, following CMH exposure (30 μM, 72 h), IPF-lung myofibroblasts showed increased Ku70 acetylation from an optical density ratio (OD) of 2.43 to 5.6 in pan-acetyl immunoblots (IB) of Ku70 immunoprecipitate (IP) (about twofold, FIG. 4D), and decreased Ku70/FLIP complex from 6.2 to 4.1 OD in FLIP-IB (about 1.5-fold, FIG. 4E). FLIP downregulation from an OD of 1.85 to 0.49 (about 3.5-fold) was detected in WB (FIG. 4F), and a 60% reduction from a mean fluorescence intensity (MFI)=$10^3$ to only $10^1$ was detected with flow cytometry (FIG. 4G). Thus, SIRT1-mediated Ku70-deacetylation stabilizes IPF-lung myofibroblast FLIP via Ku70/FLIP complex. This effect of CMH on Ku70 further disrupts Ku70/FLIP complex and destabilizes FLIP in IPF-lung myofibroblasts.

Example 5: CMH Alters Apoptosis Pathways Regulated by SIRT1/Ku70 in Human IPF-lung Myofibroblasts RNA-seq array analyses of IPF-lung fibroblasts were performed before (vehicle), and after CMH treatment (30 μM) for 72 h. Analysis of unsupervised clustering for differentially expressed SIRT1-mediated signaling genes was performed. Heat maps of gene expression normalized data that were scaled to give all genes equal variance showed decreases in SIRT1 and SIRT1-signaling with increments in E2F and caspase-9. A MetaCore pathway map (Genego Inc., St Joseph, MI, USA) revealed increased p53 phosphorylation by MAPk, increased Bax activity, Bax-mediated apoptosis cascades, p53 phosphorylate, and overexpressed PKC, which in turn phosphorylate and activate RAD pathways. The map shows CMH-mediated upregulation of E2F1 with downstream activation of Apaf-1 and upregulation of caspase-9.

Table 1 below indicates the expression of specific genes in IPF myofibroblasts of CCL-191 line incubated with CMH and the vehicle, correspondingly, calculated by $2^{-\Delta\Delta Ct}$ the data is represented as mean±standard error).

TABLE 1

| Gene | Vehicle; M ± m | CMH; M ± m |
|---|---|---|
| XRCC6 | 192.46 ± 1.92 | 84.85 ± 22.88 |
| HIC1 | 5.55 ± 0.6 | 0.68 ± 0.44 |
| SIRT1 | 3.47 ± 0.1 | 0.48 ± 0.04 |
| TP53AIP1 | 1.67 ± 0.22 | 1.11 ± 0.2 |
| TP53 | 8.14 ± 1.32 | 1.8 ± 1.19 |
| PRKCDBP | 107.67 ± 31.83 | 21.87 ± 9.21 |
| PPP1R13B | 1.72 ± 1.19 | 0.1 ± 0.05 |
| BCL2L11 | 3.28 ± 1.36 | 0.58 ± 0.09 |
| CFLAR | 7.36 ± 2.29 | 3.5 ± 1.42 |
| TP53INP2 | 12.53 ± 1.61 | 8.16 ± 0.54 |
| MCL1 | 52.13 ± 4.05 | 67.57 ± 34.04 |
| E2F1 | 0.21 ± 0.12 | 0.39 ± 0.21 |
| AIFM1 | 10.92 ± 2.11 | 12.3 ± 2.89 |
| CFLAR-AS1 | 0.09 ± 0.03 | 0.11 ± 0.04 |
| BAX | 196.43 ± 24.62 | 319.29 ± 78.06 |
| CASP9 | 0.38 ± 0.24 | 9.57 ± 6.69 |
| DIABLO | 3.32 ± 1.79 | 13.48 ± 3.27 |
| BCL2L10 | 0 ± 0 | 0.13 ± 0.05 |
| PRKCD | 6.51 ± 0.7 | 9 ± 4 |
| CASP8 | 5.4 ± 3.16 | 7.13 ± 4.18 |

Figure 5A:
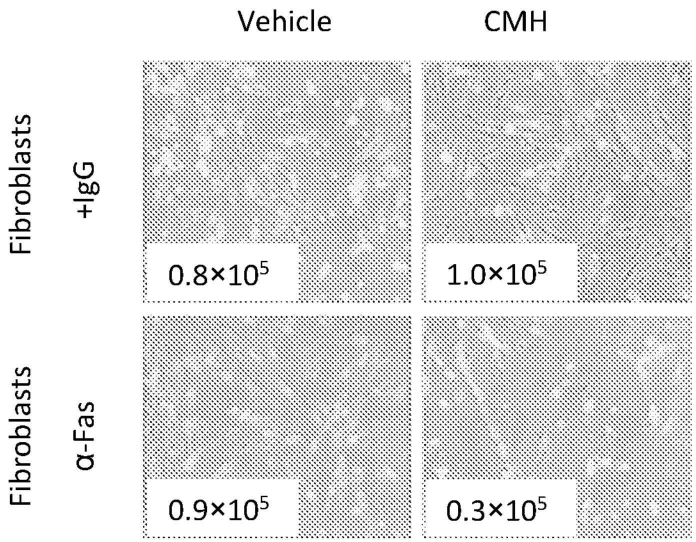
FIG. 5A-5C. CMH increases SIRT1-regulated Fas- cell death and Fas- cascades in IPF-lung myofibroblasts. Survival pathways in RNA-seq and specific gene changes of CMH (30 μM) compared to vehicle (4% DMSO) in the IPF-lung myofibroblast ATCC191 cell line.
Figure 5B:
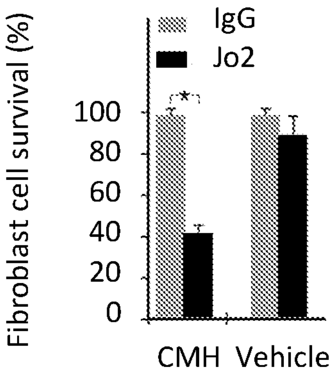
Figure 5C:
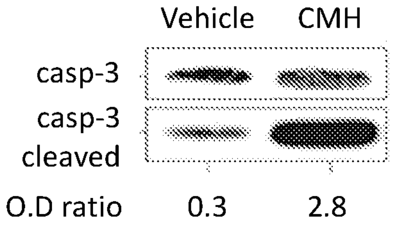

Example 6: CMH Triggers and Boosts Fas-Death Signaling in Human IPF-Lung Myofibroblasts MetaCore RNA-seq arrays of IPF-lung myofibroblasts revealed that molecular events activated by Fas to induce cell-death are triggered and amplified by CMH. The map showed positive binding interactions between Fas receptor (CD95) and its ligand (TNFSF6), as well as the FADD-caspase-8-FLASH complex. Caspase-8 activation further targets effector caspase-3 and caspase-7, a parallel extrinsic pathway, caspases 6 and 9, MAPKs, and Bim phosphorylations with binding cascades to Bax, Apaf-1, and caspase-9, allowing Bax-mediated cell death to be detected as well. Concomitantly, inhibitors of these processes, including FLIP, show negative interaction with FADD and with the inhibitors of apoptotic proteins (IAPs). The X-linked inhibitor of apoptosis protein (XIAP), in particular, showed negative interaction with caspase-9. In addition, CMH increased CH-11 anti-human Fas mAb-mediated IPF-myofibroblast cell death (24 h, 10 μM) above that produced by treatment with the vehicle alone (4% DMSO), as shown by microscope images (FIG. 5A) and trypan blue exclusion (FIG. 5A, quantification in inserts, and FIG. 5B, graphical representation), with 0.9-1×$10^5$ viable cells in control compared to only 0.3×$10^5$ cells following CMH. In fact, CMH-treated cells were 10 times more likely to undergo Fas-induced apoptosis (2.8 compared to 0.3), as determined by the OD of cleaved to uncleaved caspase-3 ratios (FIG. 5C). CMH therefore amplifies Fas signaling cascades above those induced by Fas alone. Thus, multiple intracellular anti-apoptotic signaling pathways mediated by SIRT1 and Ku70 were altered by CMH in vitro, which further enhanced Fas-apoptosis cascades.

Figure 6A:
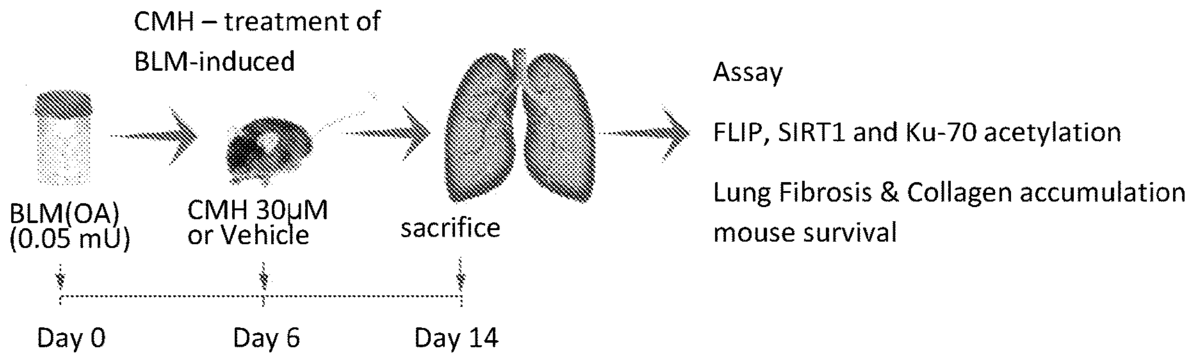
FIG. 6A-6H. CMH downregulates FLIP, increases Ku70 acetylation, decreases Ku70/FLIP complex, and attenuates fibrosis, in BLM- treated WT mouse lungs.
Figure 6B:
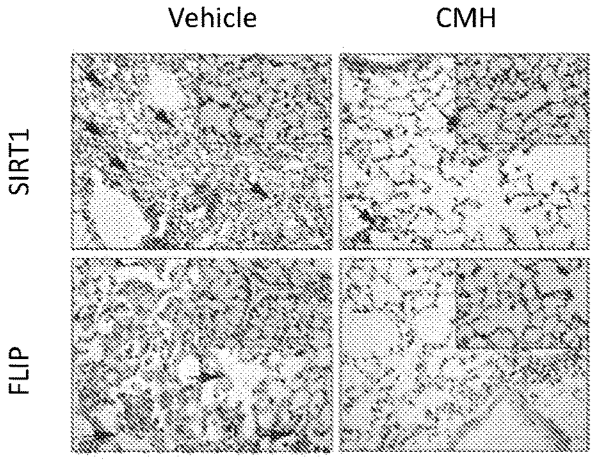
Figure 6C:
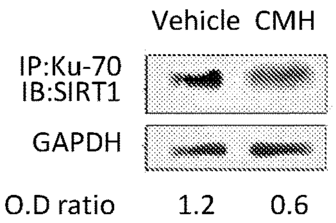
Figure 6D:
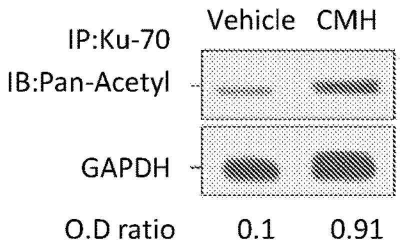
Figure 6E:
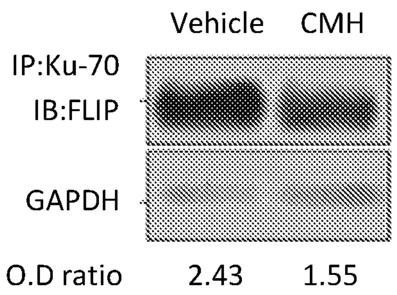
Figure 6F:
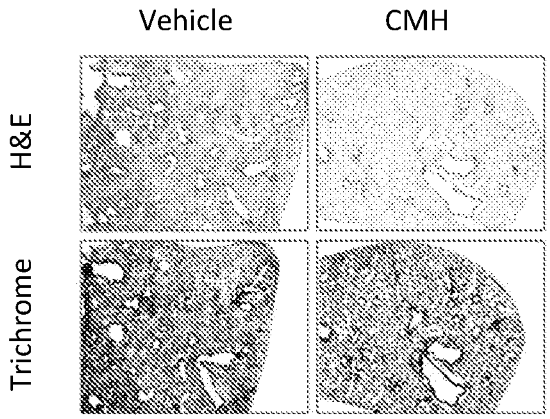
Figure 6G:
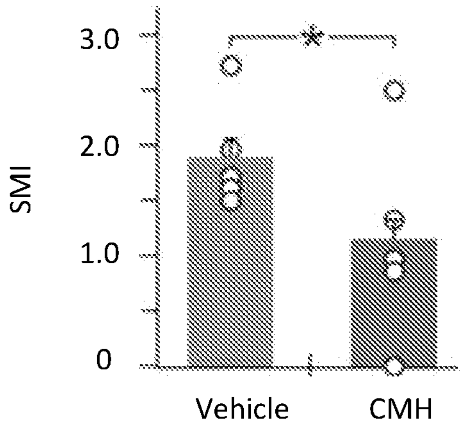
Figure 6H:
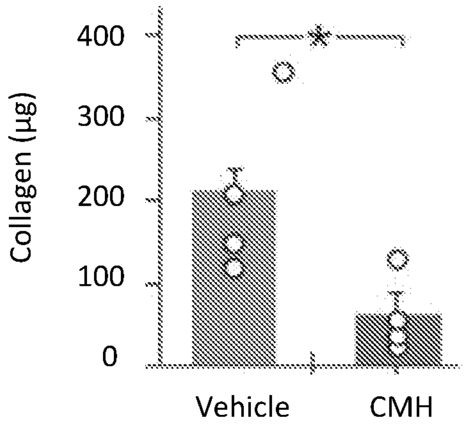

Example 7: CMH Inhibits Lung Myofibroblast SIRT1, Ku70-Deacetylation, Ku70/FLIP Complex, FLIP Expression, and Fibrosis Evolution in BLM-Treated Mice CMH (30 μM) or control vehicle 4% DMSO were administered into WT mice by a second OA on day 6 of OA-BLM (0.05 mU), or control-saline (FIG. 6A). Similar to SIRT1$^{y/y}$ mice, BLM-treated mice and control saline-treated mice (FIG. 6B) that were exposed to CMH vs. vehicle alone, had low SIRT1 and FLIP expression in lung sections. Myofibroblasts isolated from lungs of BLM-treated mice had decreased Ku70 binding to SIRT1 from 1.2 to 0.6 (FIG. 6C), increased Ku70 acetylation from an OD of 0.1 to 0.91 (FIG. 6D), and decreased Ku70/FLIP complex from an OD of 2.43 to 1.55 (FIG. 6E). Compared to vehicle, CMH-treated mice reduced H&E and collagen-trichrome staining (FIG. 6F, upper and lower panels, respectively), SMI grade (average SMI from 2 to 1.1, FIG. 6G), and collagen in Sircol assay (from 200 μg to only 50 μg, FIG. 6H). Thus, In vivo inhibition of SIRT1 activity, FLIP expression, and lung fibrosis were detected in CMH-BLM-treated mice and attenuation of deacetylation activity on Ku70, a decrease in Ku70/FLIP complex, and FLIP expression levels were detected in myofibroblasts isolated from lungs of CMH-BLM-treated mice. SIRT1-mediated Ku70-deacetylation may therefore stabilize FLIP via Ku70/FLIP complex in lung myofibroblasts promoting fibrosis, which can be inhibited by CMH.

Example 8: CMH Inhibits Cell Protein Acetylations in IPF-Lung Myofibroblasts to Comparable Levels as Detected in Normal Subjects IPF cell line ATCC191 and Normal cell line ATCC151 (0.5×$10^6$, 191 and 151, respectively), were cultured (10%

Figure 7A:
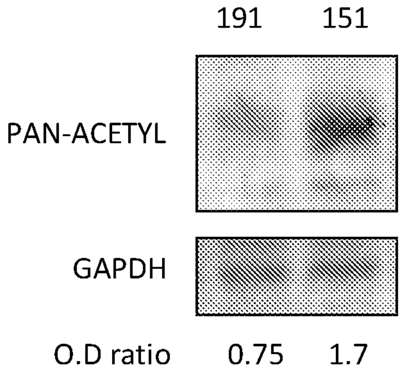
FIG. 7A-7B. CMH inhibits acetylation of cell proteins in IPF-lung myofibroblasts to comparable levels as detected in normal subjects.
Figure 7B:
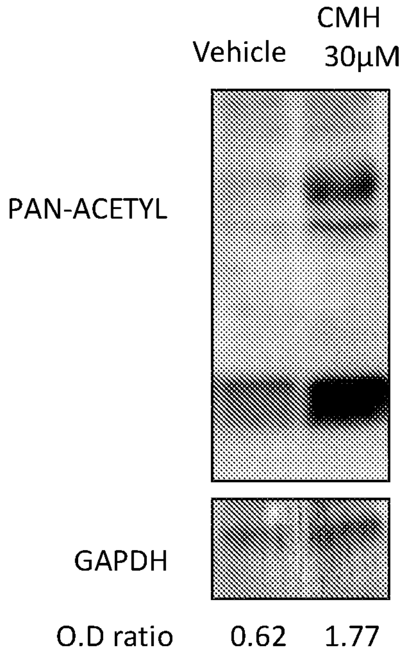

DMEM) and total cell acetylations was compared. IPF cell line ATCC191 were further exposed in culture (10% DMEM) to CMH (30 μM, vs. 4% DMSO (vehicle)). Total cell-lysate immunoblots with subsequent pan-acetyl in IPF-lung vs. normal-lung myofibroblasts (191 vs. 151) was measured (FIG. 7A). IPF-lung myofibroblasts treated with CMH were compared to control treatment with vehicle (FIG. 7B). Normal-lung, compared to IPF myofibroblasts showed increased protein acetylations from an optical density ratio to GAPDH (OD) of 0.75 to 1.7 in pan-acetyl immunoblots (FIG. 7A) and CMH diverted the low levels of acetylation to high levels (from 0.62 to 1.77 OD) as in normal subjects (FIG. 7B). Thus, CMH inhibits IPF cell proteins-deacetylation and normalized it.

Example 9: Decreased FLIP with Increased Ku70 Acetylation in Human IPF-Lung Myofibroblasts Following Exposure to a Compound of Formula 6

Figure 8A:
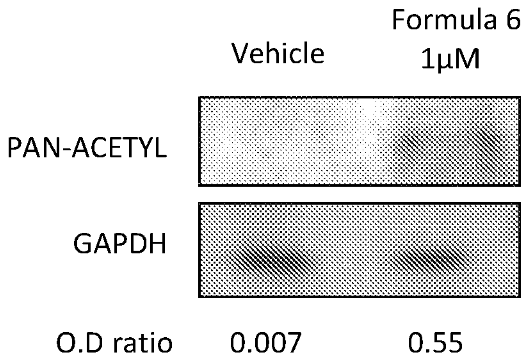
FIG. 8A-8C. Decreased FLIP with increased Ku70 acetylation in human IPF-lung myofibroblasts following exposure to a compound of Formula 6.
Figure 8B:
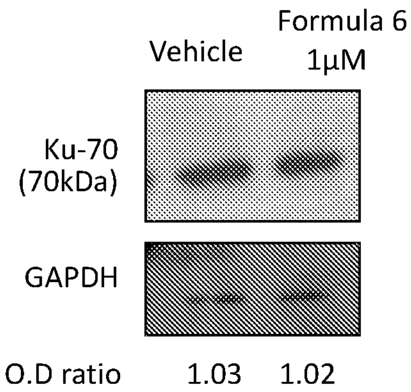
Figure 8C:
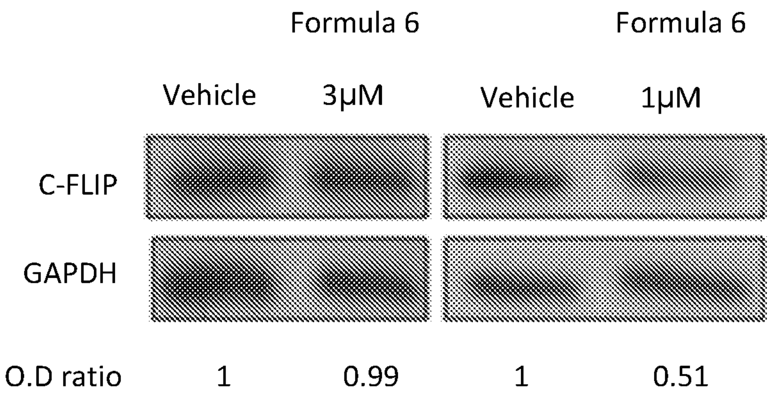

IPF cell line ATCC-191 ($0.5\times10^6$), were exposed in culture (10% DMEM) to a compound of Formula 6 (1 or 3 μM) vs. 4% DMSO (vehicle) for 16 h. Ku70 immunoprecipitation with subsequent pan-acetyl (FIG. 8A) and immunoblots of Ku70 with anti-Ku70 mAb (FIG. 8B) or FLIP with anti-FLIP mAb (FIG. 8C) were measured. IPF-lung myofibroblasts showed increased Ku70 acetylation in particular in 1 μM from an optical density ratio to GAPDH (OD) of 0.007 to 0.55 (namely by about 80-fold) in pan-acetyl immunoblots of Ku70 immunoprecipitate (FIG. 8A) without changing their Ku70 levels (FIG. 8B). IPF-lung myofibroblasts decreased FLIP expression from an OD of 1.00 to 0.51 (about twofold, FIG. 8C). Thus, a compound of Formula 6 inhibits Ku70-deacetylation to a greater extent than CMH and attenuates FLIP stabilization in IPF-lung myofibroblast.

Example 10: Lack of Direct Cytotoxicity of the Compound of Formula 6

IPF cell line ATCC-191 ($0.5\times10^6$), were exposed in culture (10% DMEM) to a compound of Formula 6 (0.1-30 μM) vs. 4% DMSO (vehicle) for 72 h. Cells were lysed and immunoblots of caspase-3 cleaved vs. uncleaved were performed. Table 2 shows that IPF-lung myofibroblasts did not change significantly in cleaved /uncleaved caspase-3 ratio between the higher concentrations of a compound of Formula 6 and control DMSO. Lower concentrations of a compound of Formula 6 treated cells even decreased their ratio indicating no toxicity of the analogue at these concentrations.

TABLE 2

| Compound [concentration] | Cleaved | Uncleaved | Cleaved/Uncleaved |
|---|---|---|---|
| Formula 6 [30 μM] | 93.19 | 37.4 | 2.49 |
| Formula 6 [10 μM] | 112.38 | 78.84 | 1.43 |
| Formula 6 [3 μM] | 81.78 | 74.31 | 1.10 |
| Formula 6 [1 μM] | 27.59 | 60.57 | 0.46 |
| Formula 6 [0.3 μM] | 11.66 | 65.84 | 0.18 |
| Formula 6 [0.1 μM] | 7.5 | 27.37 | 0.27 |
| DMSO [30 μM] | 15.36 | 8.9 | 1.73 |
| DMSO [10 μM] | 10.42 | 3.48 | 2.99 |

Thus, a compound of Formula 6, demonstrated herein to attenuate FLIP levels (Example 9), does not exert direct cytotoxic effects on cells and does not induce apoptosis in the absence of Fas or Fas-secreting cells (such as immune cells).

Example 11: Decreased FLIP in Human IPF-Lung Myofibroblasts Following Exposure to a Compound of Formula 12

Figure 9:
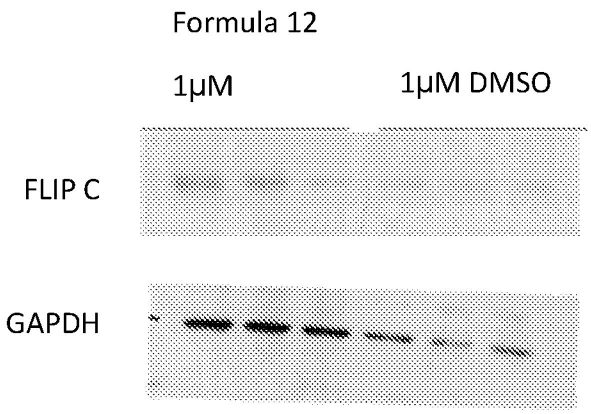
FIG. 9. Decreased FLIP in human IPF-lung myofibroblasts following exposure to a compound of Formula 12. Immunoblots of FLIP with anti-FLIP mAb of IPF-lung myofibroblasts treated with a compound of Formula 12 (1 μM) vs. vehicle.

IPF cell line ATCC-191 ($0.5\times10^6$), were exposed in culture (10% DMEM) to a compound of Formula 12 (1 μM), vs. 4% DMSO (vehicle) for 16 h. Immunoblots of FLIP with anti-FLIP mAb were performed (FIG. 9). IPF-lung myofibroblasts showed decreased FLIP levels from an optical density ratio to GAPDH (OD) of 9.5, 13.3 and 8.4 to 4.7, 3.7 and 4.8 (about twofold). Thus, the compound of Formula 12 attenuates FLIP stabilization in IPF-lung myofibroblast.

Hence, it is shown that downregulation of FLIP expression modulates fibroblast response during fibrosis evolution and resolution. Inhibition of SIRT1 and increased Ku70 acetylation, with FLIP destabilization, neutralizes resistance to apoptosis in human IPF-lung fibroblasts and enhances a variety of apoptosis cascades. Without being bound by any theory or mechanism of action, it is herein disclosed that this pathway may be used to modulate fibrosis evolution in lungs of humans with IPF.

The foregoing description of the specific embodiments will so fully reveal the general nature of the invention that others can, by applying current knowledge, readily modify and/or adapt for various applications such specific embodiments without undue experimentation and without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. The means, materials, and steps for carrying out various disclosed functions may take a variety of alternative forms without departing from the invention.

The invention claimed is:

1. A method of treating or inhibiting pulmonary fibrosis in a subject in need thereof, the method comprising administering to the subject a pharmaceutical composition comprising a therapeutically effective amount of a compound of Formula X, or salts, hydrates, solvates, polymorphs, optical isomers, geometrical isomers, enantiomers, diastereomers, or mixtures thereof:

Formula X

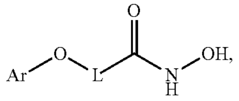

wherein L is a linker selected from the group consisting of: $C_1$-$C_{10}$ alkylene, $C_2$-$C_{10}$ alkenylene, and $C_2$-$C_{10}$ alkynylene, and Ar is selected from the group consisting of:

phenyl substituted with at least one of methyl, methoxy, amido, amino, and nitro;

$C_{10}$-$C_{18}$ fused bicyclic aryl optionally substituted with at least one of hydroxy, amido, alkylamido, amino, alkylamino, carboxyl, $CH_2CH_2OH$, and $CH_2CH_2OCH_2CH_2OH$; and $C_5$-$C_9$ fused bicyclic heteroaryl optionally substituted with at least one of hydroxy, amido, alkylamido, amino, alkylamino, carboxyl, $C_1$-$C_4$ alkyl, $C_1$-$C_4$ alkoxy, halogen, haloalkyl, nitro, cyano, $CH_2CH_2OH$, and $CH_2CH_2OCH_2CH_2OH$, provided that when Ar is $C_5$-$C_9$ fused bicyclic heteroaryl substituted with methoxy and amino, then the amino is not an aniline group.

2. The method of claim 1, wherein the fibrosis is associated with idiopathic pulmonary fibrosis (IPF).

3. The method of claim 1, wherein treating comprises alleviating a symptom of pulmonary fibrosis in the subject.

4. The method of claim 1, wherein L is a $C_2$-$C_6$ alkylene; or wherein Ar is a naphthyl; or wherein Ar is $C_5$-$C_9$ fused bicyclic heteroaryl substituted with at least one of methoxy, amido, and amino; or wherein Ar is a phenyl substituted with one substituent selected from methoxy, methyl, amido, amino, and nitro.

5. The method of claim 1, wherein the compound represented by the structure of Formula X is selected from the group consisting of:

Formula 1

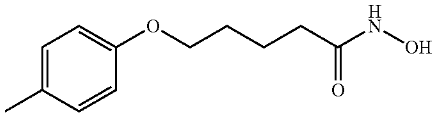

Formula 2

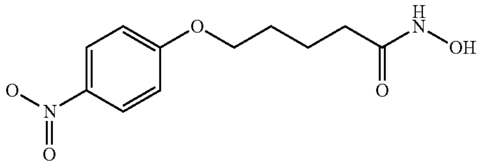

Formula 3

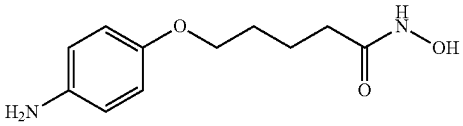

Formula 4

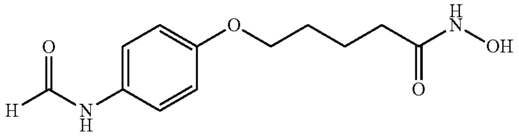

Formula 5

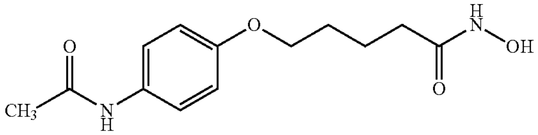

Formula 6

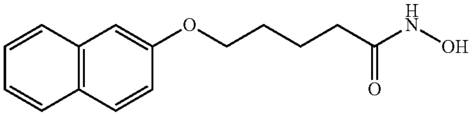

Formula 7

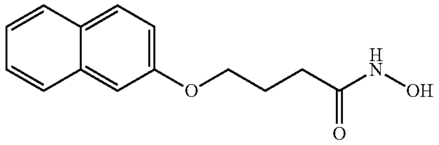

-continued

Formula 8

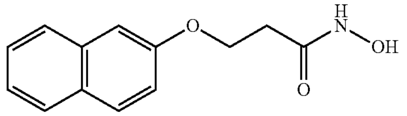

Formula 9

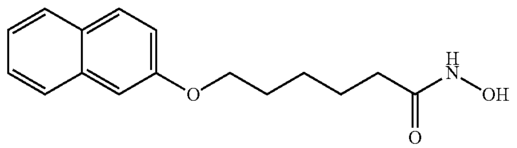

Formula 10

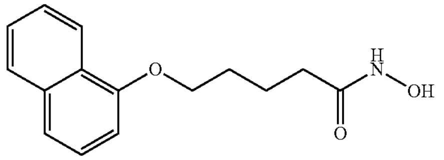

Formula 11

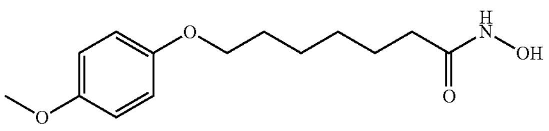

Formula 12

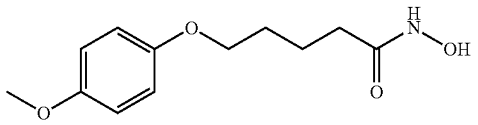

Formula 13

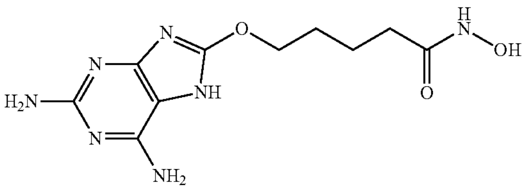

Formula 14

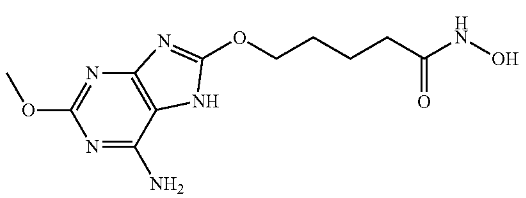

Formula 15

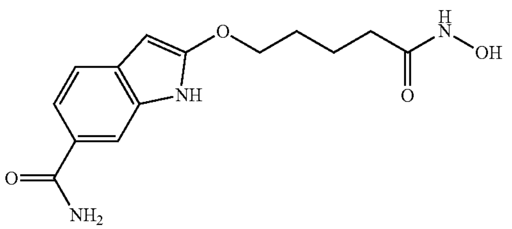

-continued

Formula 16

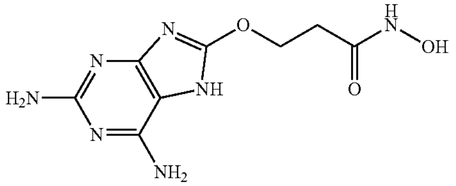

Formula 17

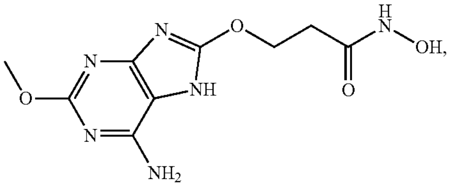

and

Formula 18

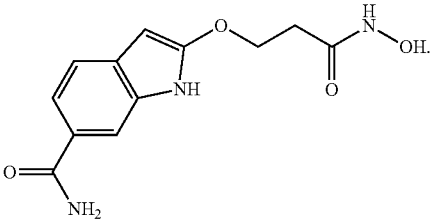

6. The method of claim 1, wherein treating comprises downregulating SIRT1-mediated deacetylase activity; or wherein treating comprises inhibiting SIRT1-mediated lysine residue deacetylation on Ku70; or wherein the compound is capable of specifically binding a binding pocket on SIRT1 protein comprising at least one of $Val^{412}$ and $His^{363}$.

7. The method of claim 1, wherein the pharmaceutical composition is in a form selected from the group consisting of tablet, pill, capsule, pellets, granules, powder, a wafer, coated or uncoated beads, lozenge, sachet, cachet, elixir, an osmotic pump, a depot system, an iontophoretic system, a patch, suspension, dispersion, emulsion, solution, syrup, aerosol, oil, ointment, suppository, a gel, and a cream; or wherein the pharmaceutical composition is adapted for administration in a route selected from the group consisting of intratracheal, intrabronchial, intra-alveolar, oral, topical, transdermal, intra-arterial, intranasal, intraperitoneal, intramuscular, subcutaneous, and intravenous, or any combination thereof.

8. A method of treating a condition associated with pulmonary fibrosis in a subject in need thereof, the method comprising administering to the subject a pharmaceutical composition comprising a therapeutically effective amount of a compound represented by the structure of Formula X, or salts, hydrates, solvates, polymorphs, optical isomers, enantiomers, diastereomers, or mixtures thereof:

Formula X

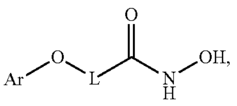

wherein L is a $C_2$-$C_6$ alkylene, and Ar is a $C_5$-$C_9$ fused bicyclic heteroaryl optionally substituted with at least one of hydroxy, amido, alkylamido, amino, alkylamino, carboxyl, $C_1$-$C_4$ alkyl, $C_1$-$C_4$ alkoxy, halogen, haloalkyl, nitro, cyano, $CH_2CH_2OH$, and $CH_2CH_2OCH_2CH_2OH$, provided that when Ar is substituted with methoxy and amino, then the amino is not an aniline group.

9. The method of claim 8, wherein the subject is afflicted with idiopathic pulmonary fibrosis (IPF).

10. The method of claim 9, wherein treating comprises alleviating a symptom of pulmonary fibrosis in the subject.

11. A method of treating a condition associated with pulmonary fibrosis in a subject in need thereof, the method comprising administering to the subject a pharmaceutical composition comprising a therapeutically effective amount of a compound selected from the group consisting of:

Formula 1

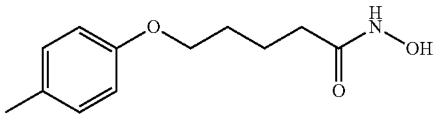

Formula 2

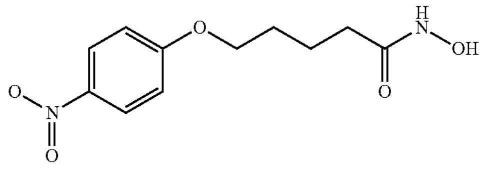

Formula 3

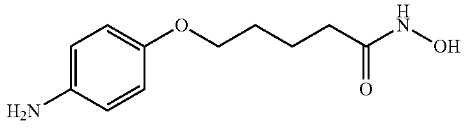

Formula 4

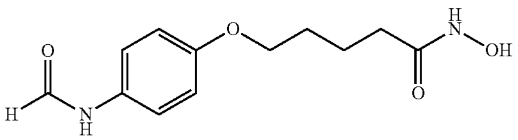

Formula 5

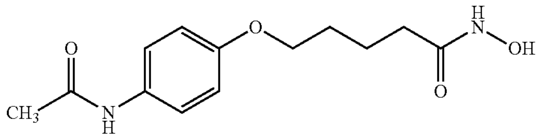

Formula 13

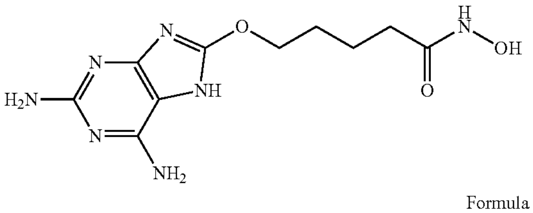

Formula 14

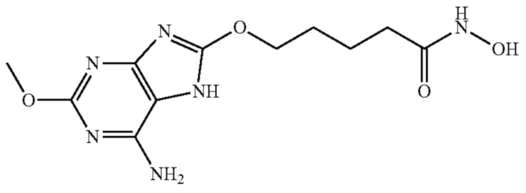

-continued

Formula 15

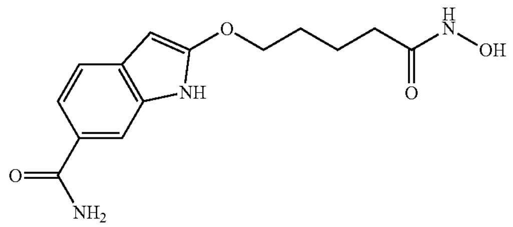

Formula 16

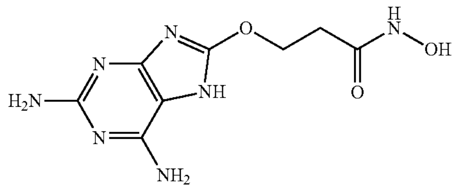

Formula 17

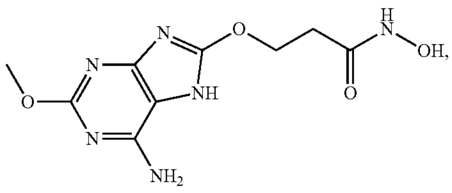

and

Formula 18

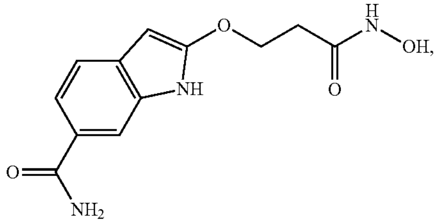

or salts, hydrates, solvates, polymorphs, or mixtures thereof.

12. The method of claim 11, wherein the subject is afflicted with idiopathic pulmonary fibrosis (IPF).

13. The method of claim 12, wherein treating comprises alleviating a symptom of pulmonary fibrosis in the subject.

14. A method of inhibiting SIRT1-mediated signaling in a cell selected from the group consisting of fibroblast, myofibroblast and epithelial cell under epithelial-mesenchymal transition (EMT), the method comprising contacting the cell with an effective amount of a compound represented by the structure of Formula X as defined in claim 1, wherein the contacting is performed in vitro, and/or wherein the cells are lung-derived cells.

15. The method of claim 5, wherein the compound represented by the structure of Formula X is Formula 6, Formula 11 or Formula 12.

16. The method of claim 15, wherein the compound represented by the structure of Formula X is Formula 6.

* * * * *